US010222378B2

(12) United States Patent
Gilbert et al.

(10) Patent No.: US 10,222,378 B2
(45) Date of Patent: Mar. 5, 2019

(54) UNITARY CARTRIDGE FOR PARTICLE PROCESSING

(71) Applicant: CYTONOME/ST, LLC, Bedford, MA (US)

(72) Inventors: John R. Gilbert, Brookline, MA (US); Hugh Lewis, Gravelotte (ZA); Derek Beaupre, Hampton, NH (US); Jaishree Trikha, Waban, MA (US); Manish Deshpande, Canton, MA (US)

(73) Assignee: CYTONOME/ST, LLC, Bedford, MA (US)

( * ) Notice: Subject to any disclaimer, the term of this patent is extended or adjusted under 35 U.S.C. 154(b) by 0 days.

(21) Appl. No.: 15/818,333

(22) Filed: Nov. 20, 2017

(65) Prior Publication Data

US 2018/0074060 A1  Mar. 15, 2018

Related U.S. Application Data

(63) Continuation of application No. 14/179,760, filed on Feb. 13, 2014, now Pat. No. 9,823,252, which is a
(Continued)

(51) Int. Cl.
*G01N 1/00* (2006.01)
*G01N 33/577* (2006.01)
(Continued)

(52) U.S. Cl.
CPC ...... *G01N 33/577* (2013.01); *B01L 3/502761* (2013.01); *B01L 3/502776* (2013.01);
(Continued)

(58) Field of Classification Search
CPC .................................................. G01N 1/00
See application file for complete search history.

(56) References Cited

U.S. PATENT DOCUMENTS 4,004,150 A   1/1977   Natelson
4,478,076 A   10/1984  Bohrer
(Continued)

FOREIGN PATENT DOCUMENTS

DE   102005054923 B3   4/2007
EP       0644417 A1    3/1995
(Continued)

OTHER PUBLICATIONS

"Applying Microfluidic Chemical Analytical Systems to Imperfect Samples", P. Yager et al., Micro Total Analysis Systems 98, D. Harrison & A. van den Berg (ed.), Kluwer Academic Publishers, Dordrecht, 207-212, 1998.
(Continued)

*Primary Examiner* — Jyoti Nagpaul
(74) *Attorney, Agent, or Firm* — McCarter & English, LLP; David R. Burns

(57) ABSTRACT

A single disposable cartridge for performing a process on a particle, such as particle sorting, encapsulates all fluid contact surfaces in the cartridge for use with microfluidic particle processing technology. The cartridge interfaces with an operating system for effecting particle processing. The encapsulation of the fluid contact surfaces insures, improves or promotes operator isolation and/or product isolation. The cartridge may employ any suitable technique for processing particles.

26 Claims, 17 Drawing Sheets

US 10,222,378 B2

Page 2

Related U.S. Application Data continuation of application No. 13/240,521, filed on Sep. 22, 2011, now Pat. No. 8,679,422, which is a continuation of application No. 11/295,183, filed on Dec. 5, 2005, now Pat. No. 8,277,764.

(60) Provisional application No. 60/633,396, filed on Dec. 3, 2004.

(51) Int. Cl.
| | |
|---|---|
| *B01L 3/00* | (2006.01) |
| *B01L 9/00* | (2006.01) |
| *C12M 1/00* | (2006.01) |
| *G01N 15/10* | (2006.01) |
| *G01N 15/14* | (2006.01) |
| *B01L 5/00* | (2006.01) |

(52) U.S. Cl.
CPC .......... *B01L 9/527* (2013.01); *C12M 47/04* (2013.01); *G01N 15/1056* (2013.01); *G01N 15/1484* (2013.01); *B01L 5/00* (2013.01); *B01L 2200/027* (2013.01); *B01L 2200/0636* (2013.01); *B01L 2200/0647* (2013.01); *B01L 2200/082* (2013.01); *B01L 2200/10* (2013.01); *B01L 2300/0809* (2013.01); *B01L 2300/0864* (2013.01); *B01L 2400/0487* (2013.01); *G01N 2015/149* (2013.01); *G01N 2015/1486* (2013.01); *Y10T 436/2575* (2015.01)

(56) References Cited

U.S. PATENT DOCUMENTS

| | | |
|---|---|---|
| 4,478,077 A | 10/1984 | Bohrer et al. |
| 4,498,353 A | 2/1985 | Kitade |
| 4,498,780 A | 2/1985 | Banno et al. |
| 4,498,782 A | 2/1985 | Proctor et al. |
| 4,501,144 A | 2/1985 | Higashi et al. |
| 4,560,865 A | 12/1985 | Bergstrom |
| 4,651,564 A | 3/1987 | Johnson et al. |
| 4,797,696 A | 1/1989 | Allen et al. |
| 4,983,038 A | 1/1991 | Ohki et al. |
| 4,987,432 A | 1/1991 | Landwehr |
| 5,050,429 A | 9/1991 | Nishimoto et al. |
| 5,082,242 A | 1/1992 | Bonne et al. |
| 5,108,623 A | 4/1992 | Cangelosi et al. |
| 5,176,358 A | 1/1993 | Bonne et al. |
| 5,216,488 A | 6/1993 | Tguunanen et al. |
| 5,244,537 A | 9/1993 | Ohnstein |
| 5,307,144 A | 4/1994 | Hiroshi et al. |
| 5,323,999 A | 6/1994 | Bonne et al. |
| 5,441,597 A | 8/1995 | Bonne et al. |
| 5,644,388 A | 7/1997 | Maekawa et al. |
| 5,683,159 A | 11/1997 | Johnson |
| 5,716,852 A | 2/1998 | Yager et al. |
| 5,726,751 A | 3/1998 | Altendorf et al. |
| 5,757,476 A | 5/1998 | Nakamoto et al. |
| 5,799,030 A | 8/1998 | Brenner |
| 5,822,170 A | 10/1998 | Cabuz et al. |
| 5,836,750 A | 11/1998 | Cabuz |
| 5,837,200 A | 11/1998 | Diessel et al. |
| 5,851,488 A | 12/1998 | Saul et al. |
| 5,863,502 A | 1/1999 | Southgate et al. |
| 5,876,266 A | 3/1999 | Miller et al. |
| 5,893,722 A | 4/1999 | Hibbs-Brenner et al. |
| 5,922,210 A | 7/1999 | Brody et al. |
| 5,932,100 A | 8/1999 | Yager et al. |
| 5,948,684 A | 9/1999 | Weigl et al. |
| 5,971,158 A | 10/1999 | Yager et al. |
| 5,972,710 A | 10/1999 | Weigl et al. |
| 5,974,867 A | 11/1999 | Forster et al. |
| 6,007,775 A | 12/1999 | Yager |
| 6,082,185 A | 7/2000 | Saaski |
| 6,097,485 A | 8/2000 | Lievan |
| 6,103,199 A | 8/2000 | Bjornson et al. |
| 6,197,575 B1 | 3/2001 | Griffith et al. |
| 6,221,226 B1 | 4/2001 | Kopf-Sill |
| 6,316,781 B1 | 11/2001 | Nagle et al. |
| 6,325,114 B1 * | 12/2001 | Bevirt .............. G01N 35/1074 141/1 |
| 6,337,740 B1 | 1/2002 | Parce |
| 6,353,475 B1 | 3/2002 | Jensen et al. |
| 6,361,672 B1 | 3/2002 | Zhu et al. |
| 6,440,725 B1 | 8/2002 | Pourahmadi et al. |
| 6,496,260 B1 | 12/2002 | Hafeman et al. |
| 6,504,607 B2 | 1/2003 | Jensen et al. |
| 6,506,609 B1 | 1/2003 | Wada et al. |
| 6,534,011 B1 | 3/2003 | Karthe et al. |
| 6,567,163 B1 | 5/2003 | Sandstrom |
| 6,592,821 B1 | 7/2003 | Wada et al. |
| 6,597,438 B1 | 7/2003 | Cabuz et al. |
| 6,602,702 B1 | 8/2003 | McDevitt et al. |
| 6,616,823 B2 | 9/2003 | Kopf-Sill |
| 6,632,400 B1 | 10/2003 | Brennen et al. |
| 6,649,403 B1 | 11/2003 | McDevitt et al. |
| 6,674,525 B2 | 1/2004 | Bardell et al. |
| 6,703,205 B2 | 3/2004 | Kopf-Sill et al. |
| 6,744,038 B2 | 6/2004 | Wang et al. |
| 6,747,285 B2 | 6/2004 | Schueller et al. |
| 6,756,019 B1 | 6/2004 | Dubrow et al. |
| 6,759,662 B1 | 7/2004 | Li |
| 6,767,706 B2 | 7/2004 | Quake et al. |
| 6,771,421 B2 | 8/2004 | Rope et al. |
| 6,808,075 B2 | 10/2004 | Bohm et al. |
| 6,838,056 B2 | 1/2005 | Foster |
| 6,930,314 B2 | 8/2005 | Jackson, III et al. |
| 6,980,303 B2 | 12/2005 | Kume et al. |
| 7,157,274 B2 | 1/2007 | Bohm et al. |
| 7,220,594 B2 | 5/2007 | Foster et al. |
| 7,298,478 B2 | 11/2007 | Gilbert et al. |
| 7,312,085 B2 | 12/2007 | Chou et al. |
| 7,355,699 B2 | 4/2008 | Gilbert et al. |
| 7,476,363 B2 | 1/2009 | Unger et al. |
| 7,569,788 B2 | 8/2009 | Deshpande et al. |
| 8,277,764 B2 | 10/2012 | Gilbert et al. |
| 2002/0055167 A1 | 5/2002 | Pourahmadi et al. |
| 2002/0071121 A1 | 6/2002 | Ortyn et al. |
| 2002/0124896 A1 | 9/2002 | O'Connor et al. |
| 2002/0177135 A1 | 11/2002 | Doung et al. |
| 2003/0027225 A1* | 2/2003 | Wada ................. B01L 3/50273 435/7.21 |
| 2003/0096430 A1 | 5/2003 | Holl et al. |
| 2003/0138941 A1 | 7/2003 | Gong et al. |
| 2004/0011650 A1 | 1/2004 | Zenhausem et al. |
| 2004/0017570 A1 | 1/2004 | Parikh et al. |
| 2004/0050866 A1 | 3/2004 | Ingenhoven et al. |
| 2004/0086872 A1 | 5/2004 | Childers et al. |
| 2004/0115094 A1 | 6/2004 | Gumbrecht et al. |
| 2004/0161772 A1 | 8/2004 | Bohm et al. |
| 2005/0183995 A1 | 8/2005 | Deshpande et al. |
| 2007/0076199 A1 | 4/2007 | Ode |
| 2008/0030865 A1 | 2/2008 | Gilbert et al. |
| 2008/0180666 A1 | 7/2008 | Gilbert et al. |
| 2008/0182338 A1 | 7/2008 | Abraham-Fuchs et al. |

FOREIGN PATENT DOCUMENTS

| | | |
|---|---|---|
| EP | 0793098 A1 | 9/1997 |
| EP | 1001326 A1 | 5/2000 |
| FR | 2865145 A1 | 7/2005 |
| JP | 60-153023 | 8/1985 |
| JP | 07-167798 | 7/1995 |
| JP | H09-509498 A | 9/1997 |
| JP | 11-108838 | 4/1999 |
| JP | 2001515216 A | 9/2001 |
| JP | 2001520377 A | 10/2001 |
| JP | 2001527220 A | 12/2001 |
| JP | 2005-524831 A | 8/2005 |
| JP | 2005-534896 A | 11/2005 |
| JP | 2006-521786 A | 9/2006 |
| WO | 95/27199 A1 | 10/1995 |
| WO | 99/19717 A1 | 4/1999 |
| WO | 99/60397 A1 | 11/1999 |

(56) References Cited

FOREIGN PATENT DOCUMENTS

| WO | 2000/06996 A1 | 2/2000 |
|---|---|---|
| WO | 2001/02846 A1 | 1/2001 |
| WO | 01/09598 A1 | 2/2001 |
| WO | 01/45843 A9 | 5/2002 |
| WO | 2003/089158 | 10/2003 |
| WO | 2003/104772 | 12/2003 |
| WO | 2003035229 A3 | 1/2004 |
| WO | 2004039500 A1 | 5/2004 |
| WO | 2004069983 A3 | 7/2005 |

OTHER PUBLICATIONS

"Design of Microfluidic Sample Preconditioning Systems for Detection of Biological Agents in Environmental Samples", Yager, H. et al., SPIE Proceedings, 3515, 252-259, 1998.
"Development of a Flow Cytometry Based Minature Chemical Fluid Analysis System Using Fluorescent Microbeads", M. Huang. et al., SPIE Biomedical Optics, BIOS 97, conference proceedings, 1997.
"Differential Blood Cell Counts Obtained Using a Microchannel Based Flow Cytometer", E. Altendorf et al., Solid State Sensors & Actuators, vol. 1, 531, 1997.
"Diffusion-Based Optical Chemical Detection in Silicon Flow Structures", B. Weigl et al., Analytical Methods & Instrumentation, .mu.TTAS 96 special edition, 1996.
"Fluorescence Analyte Sensing in Whole Blood Based on Diffusion Separation in Silicon-Microfabricated Flow Structures", B. Welgl et al., SPIE Proceedings, J. Lakowitz (ed.), Fluorescence Sensing Technology III, 1997.
"Fluorescence and Absorbance Analyte Sensing in Whole Blood and Plasma Based on Diffusion Separation in Silicon-Microfabricated Flow Structures (T-Sensors.TM.)", B. Weigl, et al., Biomedical Optics, vol. 6, No. 1, Jul. 1997.
"Implementation of Novel Optical Detection Methods for Clinically Important Blood Analytes Using Microfabricated Flow Structures (T-Sensors.TM.)", E. Altendorf & B. Weigl, MicroTAS 98, Banff, Canada, Apr. 1998.
"Integration of Microelectrodes With Etched Microchannels for In-Stream Electrochemical Analysis", R.Darling et al., MicroTAS 98, Banff, Canada, Apr. 1998.
"Microfabrication Technology for Research and Diagnostics, Silicon Microchannel Optical Flow Cytometry", E. Altendorf et al., SPIE Proceedings, Biomedical Optics 96, Jan. 1996.
"Microfluidic Approaches to Immunoassays", A. Hatch et al., SPIE conference on Micromachining and Microfabrication Symposium at Santa Clara, CA, Sep. 20-22, 1999.
"Microfluidic Diffusion Based Electrochemical Detection Using Microfabricated Flow Structures (T-Sensors.TM.)", B. Weigl, Analytical Chemistry, submitted 1999.
"Microfluidic Diffusion Based Separation and Detection", B. Weigl & P. Yager, Science, vol. 283, pp. 346-347, Jan. 15, 1999.
"Optical and Electrochemical Diffusion-Based Detection of Analytes in Complex Samples Using Microfabricated Flow Structures (T-SensorSTM)", B. Weigl, R. Darling, P. Yager, J. Kriebel & K. Mayes, Micro-and nanofabn'cated electro-optical mechanicalsystems for biomedical and environmental applications II-SPIE vol. 3606, Jan. 25-26, 1999.
"Rapid Sequential Chemical Analysis Using Multiple Fluorescent Reporter Beads", B. Weigl et al., .mu.TTAS 96 Conference Proceedings, 1996.
"Results Obtained Using a Prototype Microfluidics-Based Hematology Analyzer", E.Altendorf et al., SPIE Biomedical Optics 97, 1997.
"Silicon-Microfabricated Diffusion-Based Optical Chemical Sensor", B. Weigh & P. Yager, Reprint from "Sensors & Actuators" B 38-39, 452-457, 1997.
"Simultaneous Self-Referencing Analyte Determination in Complex Sample Solutions Using Microfabricated Flow Structures (T-Sensors.TM.)", B. Weigl et al., Proceedings of MicroTAS 98, 81-4, Banff, Canada, 1998.

"Whole Blood Assays Using Microfluidics-Based T-SensorSTm Technology", B. Weigl, Medical Design Online, http://news.medicaldesignonline.com/featuresarticles/19990416-5922.html, Apr. 1999.
Australian Examination Report dated Aug. 27, 2010 (2 pages).
Chinese Office Action for Application No. 200580046282.8, dated Dec. 21, 2011.
Cleopatra Cabuz et al., "Mesoscopic Sampler Based on 3D Array of Electrostatically Activated Diaphragms", The 10.sup.th Int. Conf. On Solid-State Sensors and Actuators, Transducers '99, Jun. 7-12, 1999, Sendai Japan, p. 1890-1.
Eric Alterndorf et al., "Results Obtained Using a Prototype Microfluidics-Based Hematology Analyzer", Department of Bioengineering, University of Washington, Box 352141, Seattle, WA 98195, dated prior to Aug. 2, 2000 pp. 73-76.
European Office Action for Application No. 05853002.3 dated Jan. 19, 2009.
Extended European Search Report for App. No. 11151431.1, dated May 2, 2012.
First Examination Report for Indian Application No. 2093/KOLNP/2007, dated Dec. 8, 2014.
http://www.micronics.net/hfilter.htm, pp. 1-3, downloaded Jun. 14, 2000.
http://www.micronics.net/mcytometry.htm, pp. 1-4, downloaded Jun. 14, 2000.
http://www.micronics.net/orcafluidics.htm, pp. 1-4, downloaded Jun. 14, 2000.
http://www.micronics.net/tsensor.htm, pp. 1-4, downloaded Jun. 14, 2000.
International Search Report for Application No. PCT/US2005/043965, dated Jul. 12, 2006.
International Search Report for Application No. PCT/US2007/010959, dated Aug. 8, 2008.
Invitation to Pay Additional Fees for Application No. PCT/US2007/010959, dated Feb. 1, 2008.
Invitation to Pay Additional Fees, Partial International Search Report for Application No. PCT/US2005/043965, dated Mar. 20, 2006.
Japanese Office Action for Application No. JP 2007-544599, dated Oct. 19, 2011.
Lehman, J. et al., "High-Frequency Modulation Characteristics of Red VCSELs", Electronics Letters, Feb. 13, 1997, vol. 33(4), pp. 298-300. Copyright 1997 IEE.
Notification of First Office Action, Chinese Application No. 200780019958.3, dated Feb. 2, 2012.
Office Action issued in Canadian Application No. 2,588,753, dated Oct. 30, 2012.
Office Action issued in Canadian Application No. 2,651,250, dated Mar. 5, 2015.
Office Action issued in Canadian Application No. 2,651,250, dated May 16, 2014.
Office Action issued in Japanese Application No. 2007-544599, dated Jan. 28, 2013.
Shapiro, "Practical Flow Cytometry", third edition, 1995, p. 237.
Strzelecka, E. et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.
T. Ohnstein et al., "Micromachined Silicon Microvalve", Proceedings of MEMS, 1990, IEEE Micro Electromechanical Systems, Napa Valley, California, Feb. 11-14, 1990, pp. 95-98.
Technical Examination Report by Brazilian Patent Office for Brazilian Application No. PI 0518824-5 published Apr. 11, 2017 in Official Bulletin No. 2414. (English Translation).
United States Office Action for U.S. Appl. No. 11/285,183, dated Sep. 27, 2011.
United States Office Action for U.S. Appl. No. 13/240,521, dated Jun. 7, 2012.

\* cited by examiner

UNITARY CARTRIDGE FOR PARTICLE PROCESSING

RELATED APPLICATIONS

This application is a continuation of and claims the benefit of priority to U.S. patent application Ser. No. 14/179,760, filed on Feb. 13, 2014, which is a continuation of and claims the benefit of priority to U.S. patent application Ser. No. 13/240,521, filed on Sep. 22, 2011, which is a continuation of and claims the benefit of priority to U.S. patent application Ser. No. 11/295,183, filed on Dec. 5, 2005, which claims the benefit of priority to U.S. Provisional Patent Application Ser. No. 60/633,396, filed Dec. 3, 2004, the contents of each application are herein incorporated by reference in their entirety.

FIELD OF THE INVENTION

The invention relates to a method and apparatus for processing particles, such as a method an apparatus for sorting particles based on predetermined characteristics.

BACKGROUND OF THE INVENTION

Conventional systems for processing particles rely on a number of separate, unintegrated components that are separately manufactured and assembled on site. Such conventional systems are unwieldy, and may suffer from potential contamination problems.

For example, in conventional particle sorting systems, the particles or cells to be sorted are suspended (the suspension) in a liquid medium that passes through a collection of reservoirs, tubes, chambers, nozzles, and/or fittings (collectively referred to herein as "fluid contact surfaces"). In conventional high-speed optical sorters, the suspension passes through a nozzle and is formed into a stream of droplets (the aerosol phase) before being captured in destination chambers. That droplet stream (aerosol) touches or contaminates any area within the system that is not explicitly sealed away from the stream, as it is difficult to otherwise guarantee that stray or improperly formed aerosol will not spatter in all directions. For this purpose all surfaces that are not explicitly sealed off from the aerosol phase are considered part of the "fluid contact surfaces."

In many applications that employ particle sorting and other particle processing, in particular clinical applications or pre-clinical research, it is important to ensure "operator isolation" and/or "product isolation". Operator isolation refers to protecting the operator from exposure to the particle suspension, for example, when there is a possibility of infectious disease agents existing within the suspension. Product isolation refers to isolation of the suspension from contamination with traces from outside the suspension, including contamination from the environment or from prior suspensions that have passed through the sorting system.

Conventional sorting systems and other particle processing systems require operation in sealed environmental chambers to provide operator isolation. However, these types of systems are difficult to service with manual operations. Conventional systems require either replacement or cleaning of all of the fluid contact surfaces in order to guarantee product isolation and the manual steps required to dismantle, clean, or replace conventional fluid contact surfaces represent a risk of breaking operator isolation.

SUMMARY OF THE INVENTION

The present invention provides a single disposable cartridge for performing a process on a particle, such as particle sorting, that encapsulates all fluid contact surfaces for use with microfluidic particle processing technology. The encapsulation of the fluid contact surfaces insures, improves or promotes operator isolation and/or product isolation. The cartridge may employ any suitable technique for processing particles.

According to a first aspect of the invention, a unitary particle processing cartridge for performing a process on a sample comprises a unitary particle processing cartridge having formed thereon a particle processing component for processing a sample and a plurality of fluid contact surfaces encapsulated in the unitary particle processing cartridge. All fluid contact surfaces in the unitary particle processing cartridge are encapsulated and sealed from an exterior environment.

According to another aspect of the invention, a particle sorting system comprises a unitary cartridge having formed thereon a particle sorting component, a particle source upstream of the particle sorting component for providing particles to be sorted to the particle sorting component, a sheath fluid reservoir for providing sheath fluid to suspend the particles and a keep chamber downstream of the particle sorting component for collecting sorted particles.

According to still another aspect of the invention, a method of processing a sample, comprises the steps of inserting a unitary particle processing cartridge in an operating machine and instructing the operating machine to perform a process on a sample sealed within the unitary particle processing cartridge.

In another aspect, a particle processing system comprises a particle processing chip comprising a plurality of microchannels and processing means for performing parallel processes on a plurality of samples, a cartridge containing a plurality of chambers and fluid paths for providing and receiving substances to and from the particle processing chip, a holder for mounting the particle processing chip to the cartridge to place the chambers and fluid paths of the cartridge in fluid communication with the microchannels and a plurality of aggregating tubes for receiving and aggregating processed samples from the microchannels.

In still another aspect, a unitary particle processing cartridge for performing a process on a sample comprises a unitary particle processing cartridge having formed thereon: a particle processing component for processing a sample, a plurality of fluid contact surfaces, comprising at least one fluid chamber and at least one fluid path, encapsulated in the unitary particle processing cartridge, wherein all fluid contact surfaces in the unitary particle processing cartridge are encapsulated and sealed from an exterior environment and chemical reagents for performing a process on the sample stored in a chamber of the cartridge.

According to another aspect of the invention, a unitary particle processing cartridge for performing a process on a sample is provided, comprising a unitary particle processing cartridge having formed thereon: a particle processing component for processing a sample; a plurality of fluid contact surfaces, comprising at least one fluid chamber and at least one fluid path, encapsulated in the unitary particle processing cartridge, wherein all fluid contact surfaces in the unitary particle processing cartridge are encapsulated and sealed from an exterior environment; and beads used for performing a bead-based depletion or detection on the sample, wherein the beads are stored in a first chamber of the cartridge.

In yet another aspect of the invention, a method of processing a sample is provided. The method comprises the steps of providing a sealed unitary particle processing cartridge and taking the sealed unitary particle processing cartridge to a biosafety hood, where the sealed unitary particle processing cartridge is loaded with a sample to be processed and a processing means for performing a process on the sample. Then, the sealed unitary particle processing cartridge is inserted in an operating machine. The operating machine is operated to effect processing of a sample sealed within the unitary particle processing cartridge using the processing means. Then, the sealed unitary particle processing cartridge is removed from the operating machine, and, in a biosafety hood, processed sample is removed from the sealed unitary particle processing cartridge.

DETAILED DESCRIPTION OF THE INVENTION

The present invention provides a unitary cartridge for performing particle processing, including particle sorting, on a sample. The present invention will be described below relative to illustrative embodiments. Those skilled in the art will appreciate that the present invention may be implemented in a number of different applications and embodiments and is not specifically limited in its application to the particular embodiments depicted herein.

As used herein, a "cartridge" refers to a collection of chambers and/or fluid pathways that are linked together as a single, unitary object that can be transported or moved as one piece. At least some of the components, such as chambers, in a cartridge may be rigidly linked, while other components, such as channels or tubes connecting chambers, may be flexibly linked.

As used herein, the term "microfluidic" refers to a system or device for handling, processing, ejecting and/or analyzing a fluid sample including at least one channel having microscale dimensions. The term "channel" as used herein refers to a pathway formed in or through a medium that allows for movement of fluids, such as liquids and gases. The term "microchannel" refers to a channel preferably formed in a microfluidic system or device having cross-sectional dimensions in the range between about 1.0 µm and about 250 µm, preferably between about 25 µm and about 150 µm and most preferably between about 50 µm and about 100 µm. One of ordinary skill in the art will be able to determine an appropriate volume and length of the microchannel. The ranges are intended to include the above-recited values as upper or lower limits. The microchannel can have any selected shape or arrangement, examples of which include a linear or non-linear configuration and a U-shaped configuration.

Figure 1:
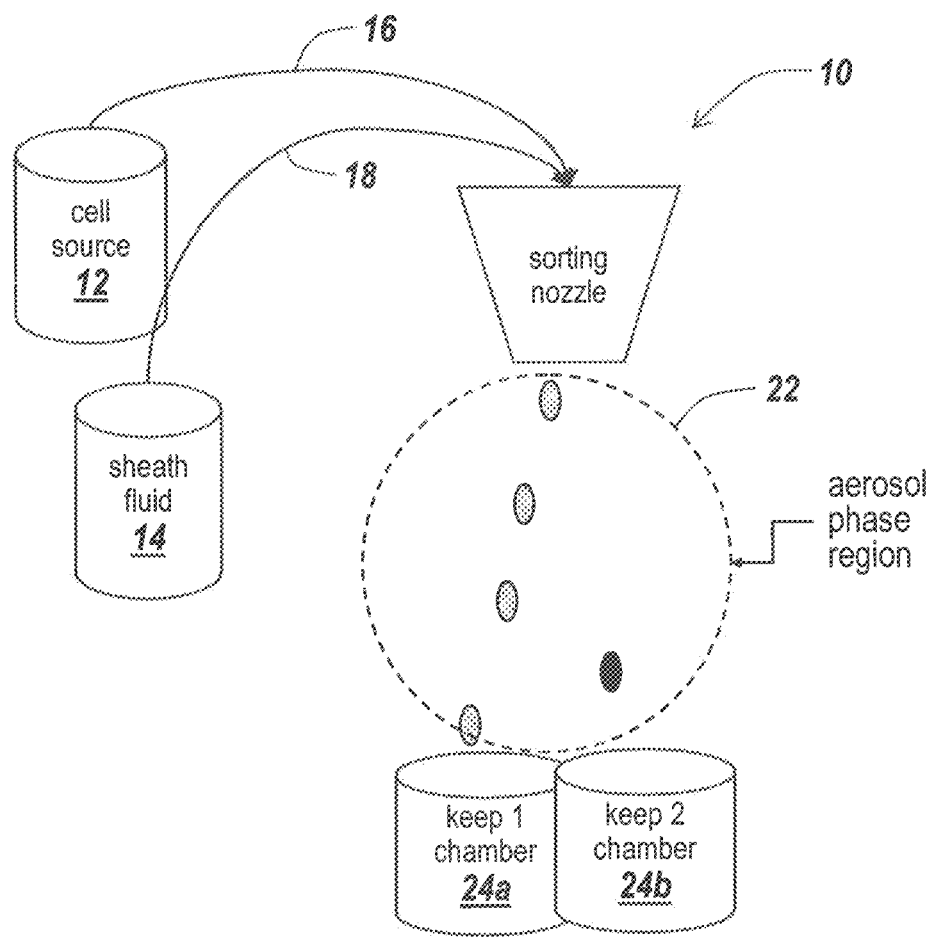
FIG. 1 illustrates a particle sorting system of the prior art.

FIG. 1 is a general schematic of fluidic contact surface systems in a conventional particle sorting system of the prior art. As shown, a conventional system 10 includes a cell source 12 and a reservoir of sheath fluid 14, which are used to establish a well behaved core flow of suspended particles. Tubes 16, 18 connect the cell source 12 and sheath chambers 14 to a sorting nozzle 20. An aerosol phase region 22 of droplets is produced by the sorting nozzle 20, followed by one or more capture chambers 24a, 24b (labeled keep1 or keep2), into which selected subsets of cells or particles are directed.

In the conventional sorting system 10 of FIG. 1, fluidic contact surfaces include at least seven different components, as well as all surfaces contiguous to the aerosol phase region 22, because droplets can spatter in all directions during initiation of flow or flow blockage events. Of necessity, in this type of conventional system 10, the "keep" chambers 24a, 24b must be open chambers in order to be accessible to droplets. The open chambers may introduce or increate contamination or expose an operator to the material within the chambers. Fluid may be driven out of the cell source 12 and sheath reservoir 14 using a pneumatic (gas) pressure applied through an external port (not shown) on those reservoirs. The pressure port can be locked by sterile filters, which present additional objects to be cleaned or disposed.

The components of the conventional sorting system 10 are typically separately movable elements that are not sealed from each other or the environment. Nor are the separate components built on the same substrate.

Throughout the application, similar components of different embodiments of the unitary particle processing cartridge may be designated with like reference numbers.

Figure 2:
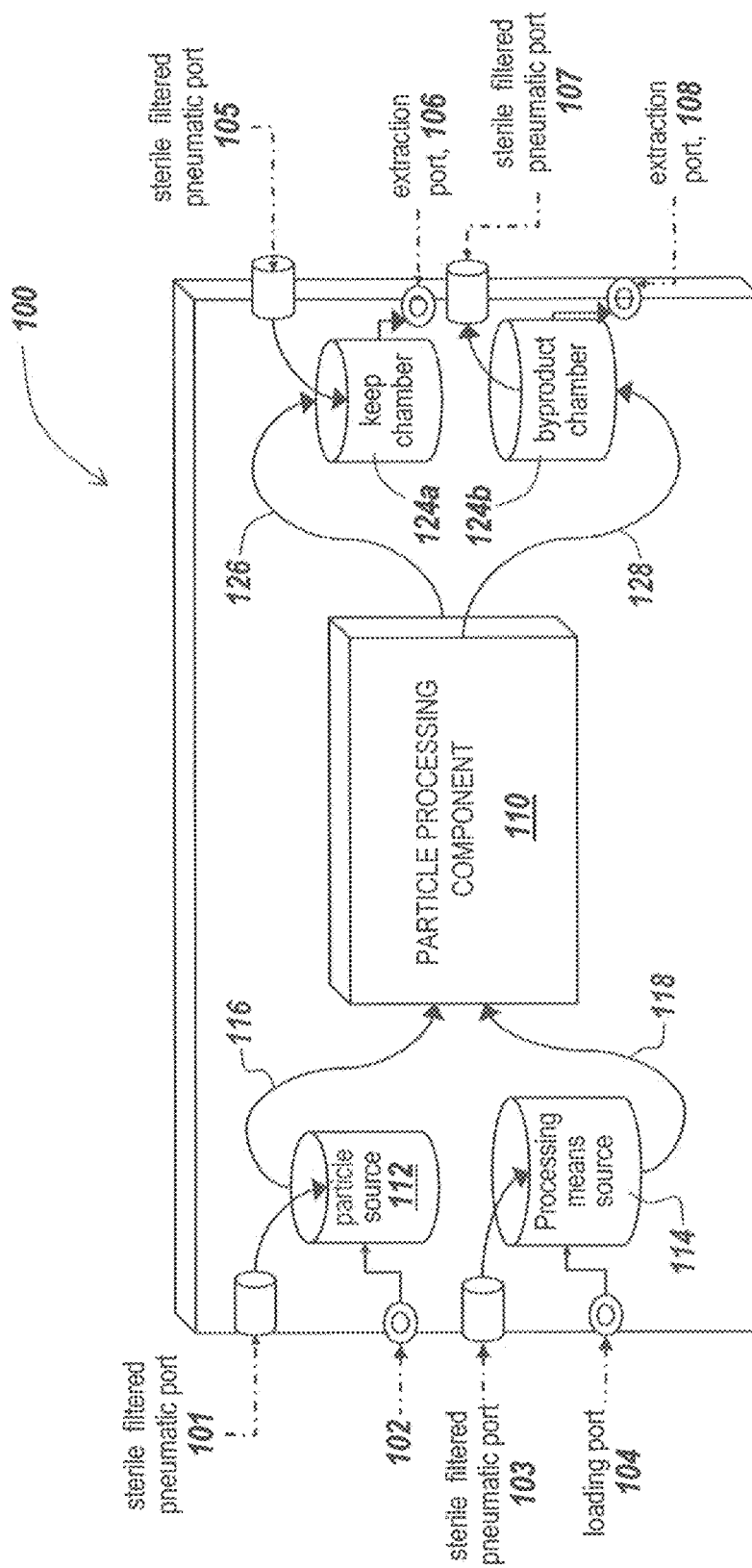
FIG. 2 illustrates a unitary cartridge for particle processing according to an illustrative embodiment of the invention.

FIG. 2 illustrates a particle processing cartridge 100 for performing a process on a sample, having many, and preferably all, fluid contact surfaces encapsulated according to an illustrative embodiment of the invention. The illustrative unitary particle processing cartridge 100 can be designed to perform any suitable process or multiple processes on a sample. Preferably, the unitary particle processing cartridge performs a microfluidic process on a sample. The cartridge may contain one or more particle processing subsystems 110 enabling one or more unit processes to be applied to a sample, such as a suspension, loaded into the cartridge 100. The particle processing subsystem 110 may be separately inserted into and removable from the cartridge 100, or may be integrally formed on the cartridge substrate. For example, the cartridge substrate may have formed therein a recess or chamber for receiving the particle processing subsystem 110. Some examples of unit processes that may be incorporated into a unitary cartridge 100 include, but are not limited to, incubation or staining of particles, washing of particles, including variants where supernatant is purified, heating or cooling of particles in a suspension, mixing cells or other particles with chemicals or beads, size-based filtering of particles, depletion or enhancement of a subset of particles in the suspension, sorting of particles, and other suitable processes known in the art.

Ideally, in order to prepare particles, such as cells for research or clinical applications, using a unitary cartridge 100 of the illustrative embodiment of the invention, a user loads the "source", such as a cell suspension, into the cartridge via a sample input port 102, operates the cartridge using the processing subsystem 110 and extracts the final product in as finished a condition as possible via a processed sample output port 106. If a processing means, such as a sheath fluid, solution, mixing suspension, magnetic beads and so on, is necessary, the processing means may be loaded into the cartridge 100 via a processor input port 104 and stored in a processing means source 114. Alternatively, a single port can serve as both the sample input port and the processor input port. An extraction port 108 may be used to access byproducts of the processing subsystem 110.

A plurality of chambers disposed between the ports and the subsystem 110 may also be provided. Preferably, at least some of the chambers are rigidly connected to each other to form the unitary cartridge 100. As shown, the illustrative cartridge 110 includes a sample input chamber 112 for storing a sample to be processed, which may be provided by the sample input port 102. The sample input chamber 112 is in fluid communication with the processing subsystem 110 via a fluid path 116. A processing means input chamber 114 may store a processing means provided via processor input port 104. A fluid path 118 fluidly connects the processing means input chamber 112 to the particle processing component 110. A processed sample chamber, illustrated as "keep" chamber 124a, stores a sample processed by the processing subsystem 110, and may be fluidly connected to the particle processing component 110 via a fluid path 126. A sample output port, such as extraction port 106 may be used to retrieve the sample from the processed sample chamber. A byproduct output chamber, illustrated as a "keep" chamber 124b, may store a byproduct of the process performed using the subsystem, such as unselected particles in a sorting system, or a byproduct solution for another process, which may be provided to the byproduct output chamber 124b from the particle processing component 110 using another fluid path 128. A plurality of pneumatic ports 101, 103, 105 and 107 in communication with the fluid paths applies pressure to facilitate fluid flow through the cartridge. In addition, a plurality of additional ports, chambers and fluid paths may be provided in the cartridge, depending on the type of process performed.

A variety of processes may be performed using the unitary cartridge 100 of the illustrative embodiment of the invention. For example, a unitary particle processing cartridge of an illustrative embodiment of the invention may be used to perform incubation or staining of particles. For example, in one application using the unitary particle processing cartridge, suspensions may be mixed and incubated with solutions containing fluorophore-labeled anti-CD4 mouse-antibodies in order to selectively label cells expressing CD4 on their surfaces.

In another application, the unitary particle processing cartridge 100 may be used for washing of particles in a suspension, including variants where supernatant is purified. For example, after the incubation, as described above, it may be desirable to remove unbound antibodies so that unbound fluorophore does not interfere with optical means for identifying the CD4 positive cells. Washing of particles in a suspension can be done in the unitary particle processing cartridge 100 by pumping the suspension from an initial chamber through a filter to separate the cells from the supernatant. Then, the extracted cells may be passed back into the original chamber, while the supernatant is passed through another chamber in the cartridge containing bound protein A or anti-mouse antibodies to precipitate any antibodies remaining in the supernatant before the purified supernatant is added back to the original chamber. This process can continue to cycle through the cartridge until the unbound antibody has been adequately removed from the supernatant.

In another application, the unitary particle processing cartridge 100 may perform heating and/or cooling of a suspension loaded therein. For example, an operating machine may provide heating and/or cooling pads or regions to the cartridge, so that each chamber or region of the cartridge may be held at different temperatures or have its temperature modified during operation of the unitary particle processing cartridge. Any suitable means for controlling the temperature within a selected chamber or region of the unitary particle processing cartridge may be used.

In another application, the unitary particle processing cartridge 100 may perform mixing of particles, such as cells, with chemicals, beads or another substance. For example, a cell suspension in a first chamber of the cartridge 100 may be pumped or driven into a second chamber containing chemicals, beads or solutions containing chemicals or beads. The second chamber may contain rotors or stir bars that may be driven by magnetic or mechanical means by the operating machine in order to enhance or control mixing.

In still another application, the unitary particle processing cartridge 100 may perform size-based filtering of particles, such as cells. For example, a cell suspension in a first chamber of the cartridge may be pumped into a second chamber through a filter, which permits only cells or particles below a certain size to flow into the second chamber. This operation produces a size defined sub-population of cells in the second chamber.

In another application, the unitary particle processing cartridge 100 may perform magnetic bead cell subset depletion or enhancement. For example, a cell suspension in a first chamber in the cartridge may be pumped into a second chamber containing magnetic beads coated with anti-CD4 antibodies, so that cells expressing CD4 on their surface will bind to the beads. After mixing in the second chamber, a magnetic field is applied by an external operating machine to the second chamber in the unitary particle processing cartridge. The magnetic field precipitates the beads, and any cells bound to the bead, to the wall of the second chamber. Then, the liquid and remaining cells in suspension are pumped into a third chamber in the cartridge, which then contains a population that is depleted for cells expressing CD4. A liquid may be then added to the second chamber to release the magnet, thus allowing the bead-bound cells to go back into suspension (with the beads). After suspension of the bead-bound cells, the resulting suspension may be pumped into a fourth chamber on the cartridge, which will then contain a population of cells enhanced for those expressing CD4.

One skilled in the art will recognize that the invention is not limited to magnetic bead cell subset depletion or enhancement, but can encompass any suitable process for depleting or enhancing bead cell subsets. For example, in one application of the unitary particle processing cartridge, a cell suspension in a first chamber may be pumped into a second chamber containing large latex beads, preferably more than 50 microns diameter, that are coated with anti-CD4 antibodies, so that cells expressing CD4 on their surface will bind to the beads. After mixing of the cell suspension and the beads in the second chamber, the resulting suspension is pumped into a third chamber through a size separation filter that allows particles smaller than 40 microns to pass and recycles larger clumps into the second chamber. The third chamber then contains a population that is depleted for cells expressing CD4. If liquid containing a chemical or enzyme that breaks the binding between the beads and the anti-CD4 antibodies is then added to the second chamber, the bound cells can be re-suspended and that suspension may be pumped into a fourth chamber which will then contain a population of cells enhanced for those expressing CD4.

According to still another application, a unitary particle processing cartridge 100 may be used to perform release testing of a product or substance. For example, a filter in the cartridge may trap a product or substance of interest, such as bacteria, in a sample that flows through the filter. The trapped bacteria may then be collected from the filter for testing.

The unitary particle processing cartridge 100 may include a plurality of sample processing subsystems 110 in the cartridge. For example, two or more sample processing subsystems 110 may be disposed in series on the cartridge to allow sequential processing of a sample. An enrichment region between the serial processing subsystems may allow for resetting of sample parameters between processes. An example of a suitable enrichment region between two sample processing stages 110 is found in U.S. application Ser. No. 10/329,008, the contents of which are herein incorporated by reference. For example, the enrichment region may be formed by a filter disposed between the sample processing subsystems on the cartridge.

Figure 3:
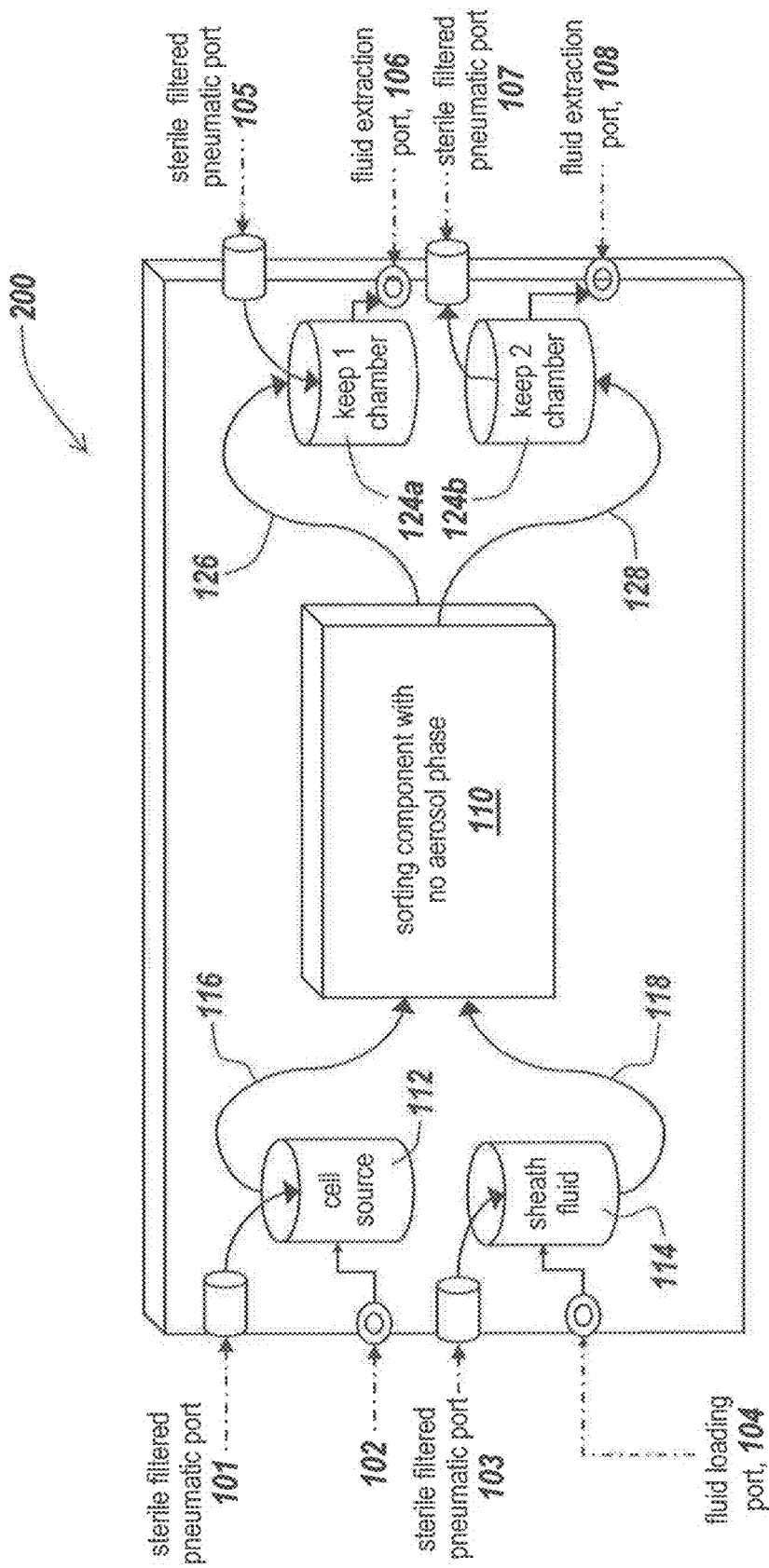
FIG. 3 illustrates a unitary cartridge for particle sorting according to an illustrative embodiment of the invention.

According to another embodiment, a unitary particle processing cartridge may be used for particle sorting. The illustrative cartridge 200 performs cell sorting, though one skilled in the art will recognize that the cartridge 200 may perform sorting on any type of particle. FIG. 3 illustrates a unitary particle sorting cartridge 200 including a microfluidic based sorting component 120 for sorting particles without an aerosol phase according to an illustrative embodiment of the invention. Upstream of the sorting component 120, the cartridge 200 includes a cell source 112 for storing particles to be sorted, a sheath fluid source 114 storing a sheath fluid for facilitating a sorting process, a sterile filtered pneumatic port 101 for the cell source, a sample loading port 102 for the cell source, a sterile filtered pneumatic port 103 for the sheath fluid and a fluid loading port 104 for the sheath fluid reservoir 114. The pneumatic ports 101, 103 apply pressure to induce or facilitate fluid flow through the cartridge. Channels, illustrated as tubes 116 and 118, connect the cell source 112 and sheath fluid reservoir 114, respectively, to inlets of the sorting component 120. Downstream of the sorting component 120, the cartridge includes keep chambers 124a, 124 for collecting sorted particles, tubes 126, 128 connecting the outlets of the sorting component 120 to the keep chambers 124a, 124b. The cartridge also includes an extraction port 106, 108 for each keep chamber 124a, 124b, respectively, for extracting collected fluid from each keep chamber, and sterile fluid pneumatic ports 105, 107, respectively. The cartridge processes relatively large volumes (0.1 ml to 5000 ml of suspension) and equal or larger volumes of sheath fluid through the system and out into output chambers 124a, 124b.

The sorting component 120 can be any suitable device for sorting particles based on a predetermined characteristic. Examples of a suitable cell sorting device include a microfluidic sorting chip, as described in U.S. Pat. No. 6,808,075 and U.S. patent application Ser. Nos. 10/329,008 and 10/664,587, the contents of which are herein incorporated by reference. However, the invention is not limited to use of a cell sorting component described in these references.

The sorting component 120 may be separately manufactured, stored, and/or shipped, and subsequently inserted into the cartridge substrate 200, creating a flexible connection. Alternatively, the sorting component 120 may be integrally and rigidly formed on the cartridge substrate 200.

As shown, fluidic connections from the cell source 112 or sheath reservoir 114 to the sorting component 120 and from the sorting component to the keep chambers 124a, 124b, can be made with single tubes or arrays of tubes. The tubes creating the fluid paths can be of any appropriate diameter.

An embodiment of a unitary particle processing cartridge of the present invention, such as the unitary particle processing cartridge 100 shown in FIG. 2 or the unitary particle sorting cartridge 200 of FIG. 3 has several properties that are improvements in operation of a cell or particle sorting system. For example, most, and preferably all, of the fluid contact surfaces are built into one object ("the cartridge"). The unitary cartridge including all the fluid contact surfaces can be inserted into a processing instrument (the platform containing sorting optics, electronics, control software and other subsystems the suspension never contacts) with a single operation. The unitary cartridge can also be disposed of in a single operation after use. The cartridge can be sterilized after assembly all at once. The cartridge can be shipped to the user in a sterile, ready to use form. Each cartridge (and therefore all fluid contact surfaces needed for a single processing run) can be given a barcode or other unique identification, making all of the parts that represent possible sources of product contamination fully traceable. In addition, no fluid waste needs to be removed from the cartridge in operation. Rather, fluid waste can be disposed of with the disposal of the cartridge, without requiring separate handling of the fluid waste.

Use of a unitary particle processing cartridge of the present invention can enhance operator and product isolation. To use the cartridge to perform a particle processing operation, such as particle sorting, a user can receive the cartridge sealed and sterile from the manufacturer. The user may then take a cartridge to a biosafety hood, such as a sterile laminar flow hood, and perform a sterile operation (in the manner of conventional tissue culture for that type of sample) to load cell sample and sheath reservoirs. The cartridge is preferably sealed before and after this operation. The user places the cartridge in the sorting instrument platform. The system sorts the cells or particles in the sample into one or more of the keep chambers in the cartridge. The user removes the cartridge from the system and takes the cartridge back to the biosafety hood to remove the processed samples through their extraction ports. The user may then dispose of the used cartridge and unneeded fluids in a safe manner. Similar steps may be taken to perform other processes on a sample using a unitary particle processing cartridge.

Figure 4:
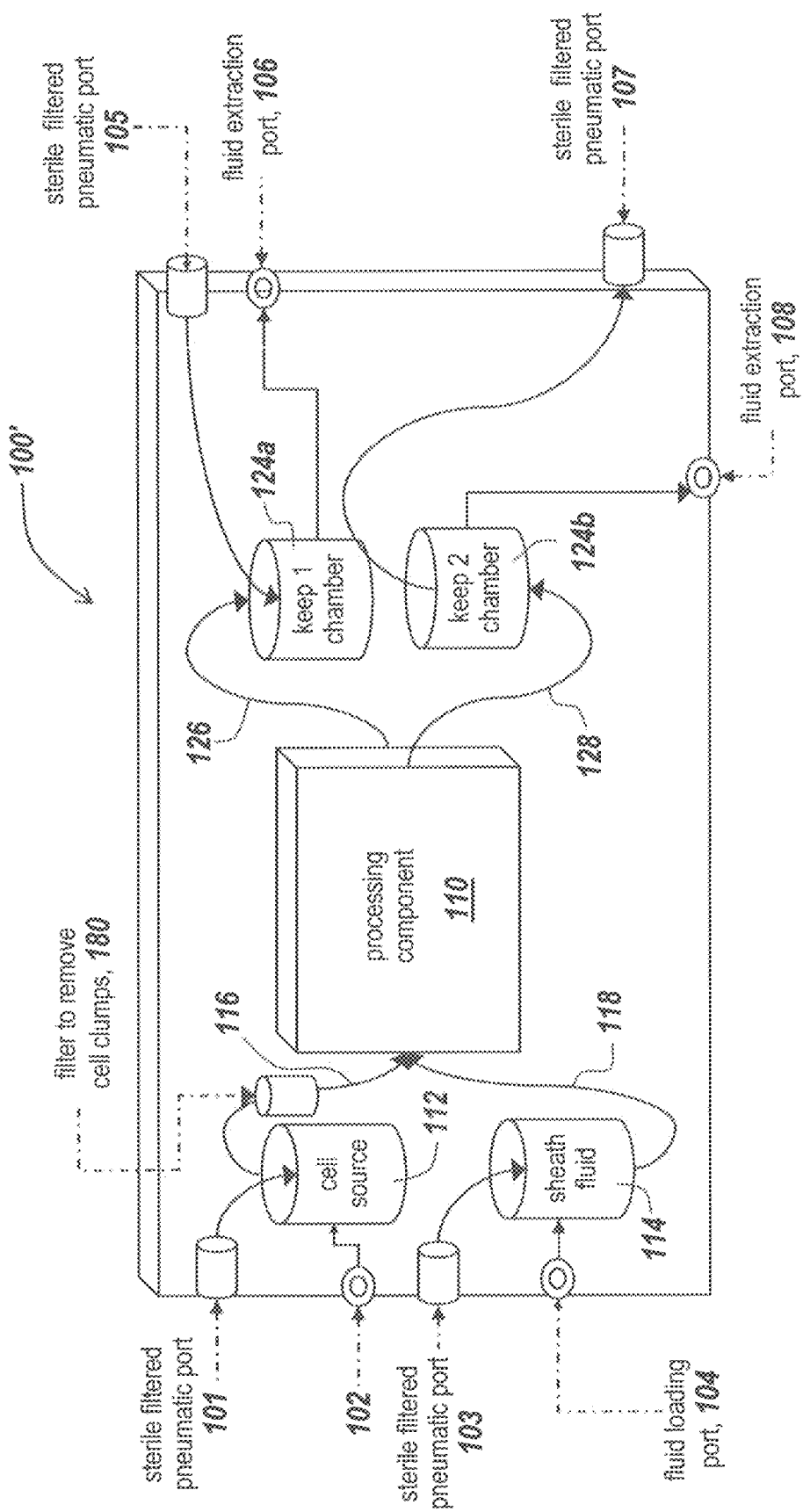
FIG. 4 illustrates a unitary particle sorting cartridge of an embodiment of the invention including an aggregation filter.

As shown in FIG. 4, a unitary particle processing cartridge 100' of an embodiment of the invention may include also an aggregation filter 180 to help remove clumps of cells and prevent clogging of the sorting component. As shown, the aggregation filter 180 can be added to the fluid line(s) 116 connecting the cell source 112 to the processing component 110. The aggregation filter 180 may comprise any suitable material suitable for filtering a sample and may be disposed in any location along a fluid flow path in the cartridge 100'.

Figure 5:
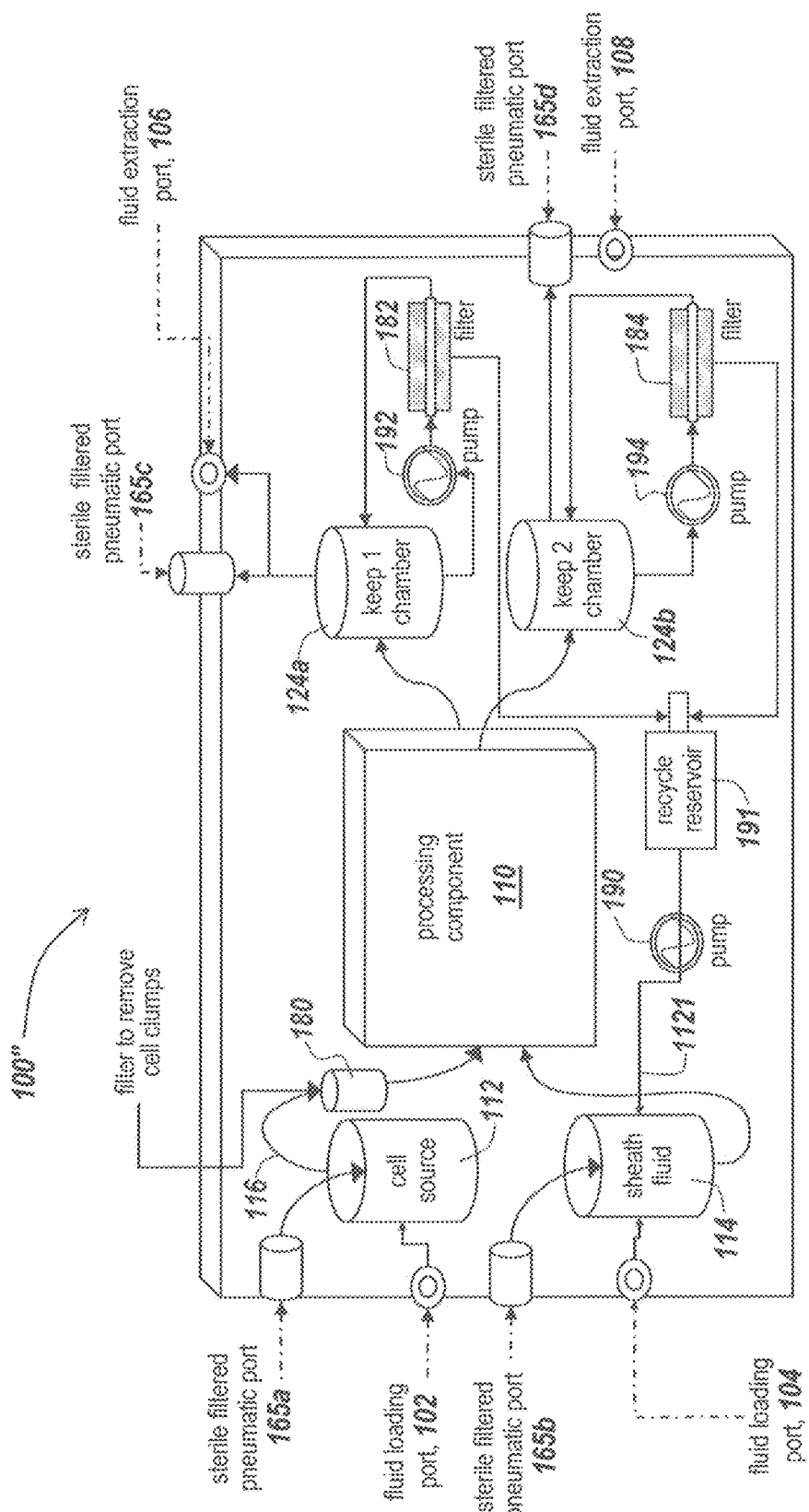
FIG. 5 illustrates a unitary particle sorting cartridge of another embodiment of the invention including pumps and filters for controlling liquid level and/or the concentration of sheath fluid, as well as providing sheath recycling.
Figure 6A:
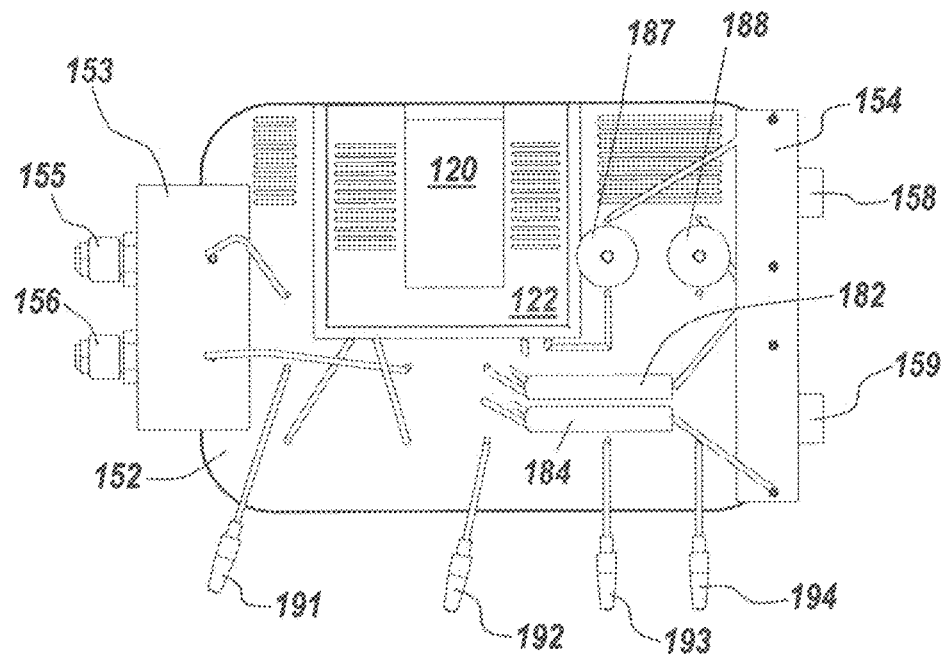
FIGS. 6A-6D are CAD drawings of an embodiment of a unitary cartridge for particle processing.
Figure 6B:
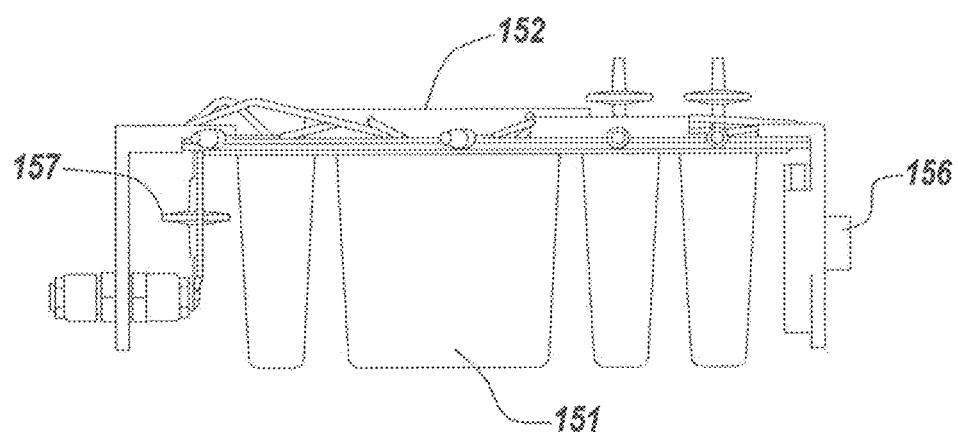
Figure 6C:
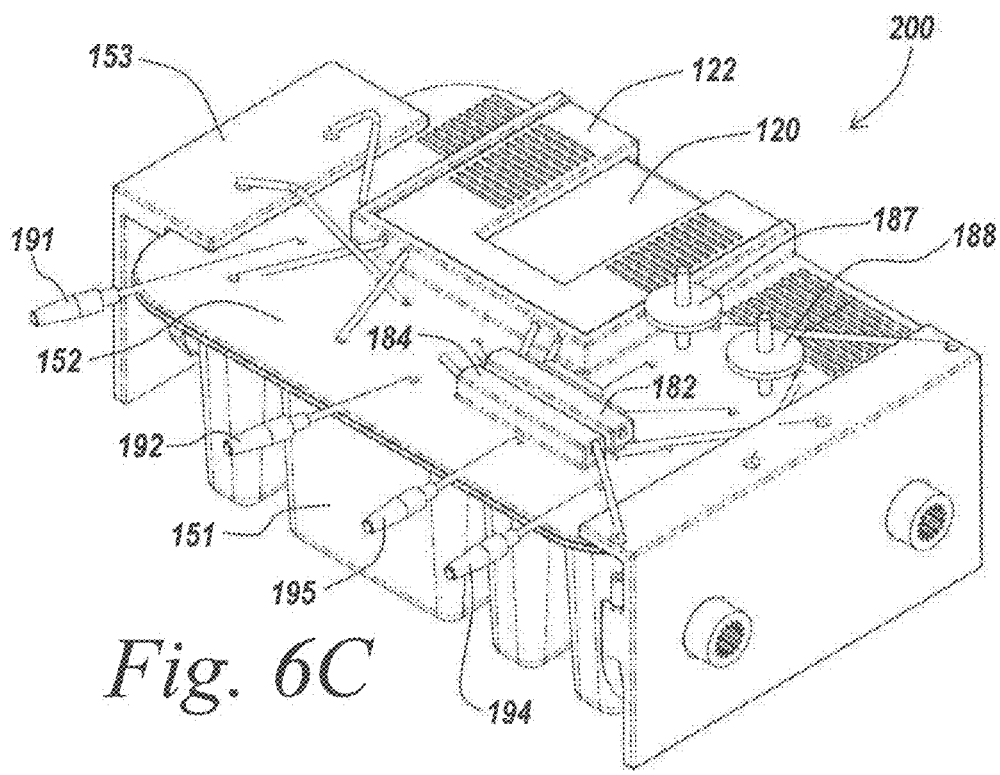
Figure 6D:
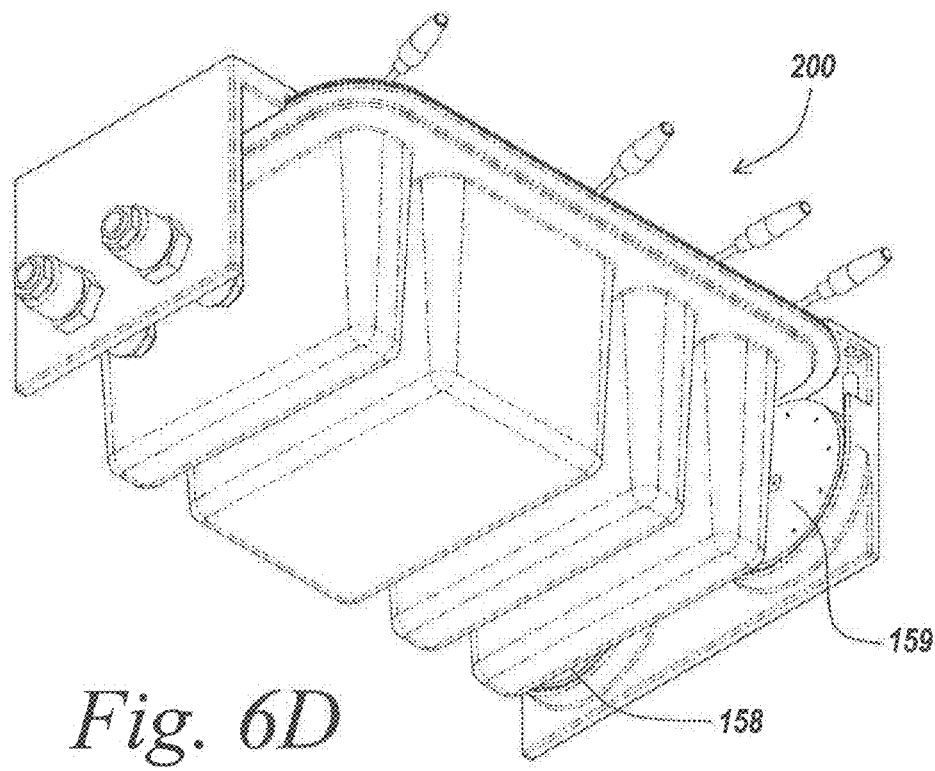

As shown in FIG. 5, a unitary particle processing cartridge 100" of another embodiment of the invention may include a component for liquid level/concentration control and sheath recycling after performing particle processing using the processing component 110. The illustrative cartridge 100" includes a pump 192, 194 and a filter 182, 184 downstream of each processed particle chamber 124a, 124b, respectively, that receives processed particles from the processing component. The pumps 192 and 194 and filters 182, 184 facilitate liquid level/concentration control and recycling of a processing means, such as sheath fluid, used to process the particles. The filters 182, 184 may be three-port flow filters, for example, hollow fiber filters, for removing fluid, such as sheath fluid, from a fluid path (i.e., the corresponding processed particle chamber 124). The system thus removes sheath fluid from the processed particle chambers to raise the concentration of collected particles in the processed particle chambers and to control the level of liquid in each processed particle chamber 124a, 124b.

The illustrative unitary particle processing cartridge 100" also includes a recycling component for recycling fluid collected by the filters 182, 184. As shown, the excess fluid may be recovered (recycled) and returned into the processing medium reservoir 114, for example, a sheath fluid reservoir, using a recycling path 1121, recycling reservoir 191 and a pump 190. The recycling reservoir 191 receives the removed fluid from the filters 182 and 184, and the pump 190 returns the extracted fluid from the filters 182 and 184 to the chamber 114 via fluid path 1121 for reuse during subsequent particle processing procedures.

FIGS. 6A-6D are CAD drawings of an embodiment of unitary particle processing cartridge 200 for particle sorting. Each cartridge is formed by a reservoir tray 151 and a reservoir cover 152. A pressure system 153 includes pressure inlets 155, 156 for applying a pressure to induce fluid flow through the fluid paths. A pumping system 154 also facilitates fluid flow and includes pump heads 158, 159. A filter 157 in the fluid path upstream of the sorting component 120 helps prevent clogs. Concentrating filters 182, 184 downstream of the keep chambers help control fluid concentration levels and facilitate recycling of sheath fluid. Valves 191, 192, 193 and 194, which may be luer-activated, interface with the cell source, sheath reservoir and keep chambers to inject or remove fluid from the cartridge. Vents 187, 188 may also be provided. As shown, the cartridge 200 has a holder 122 forms a shaped region or recess for receiving a processing component, illustrated as a sorting component 120, such as the sorting chips described in U.S. Pat. No. 6,808,075 and U.S. patent application Ser. Nos. 10/329,008 and 10/664,587, which are incorporated herein by reference. The invention is not limited to the sorting chips or processes described in these references.

Figure 7:
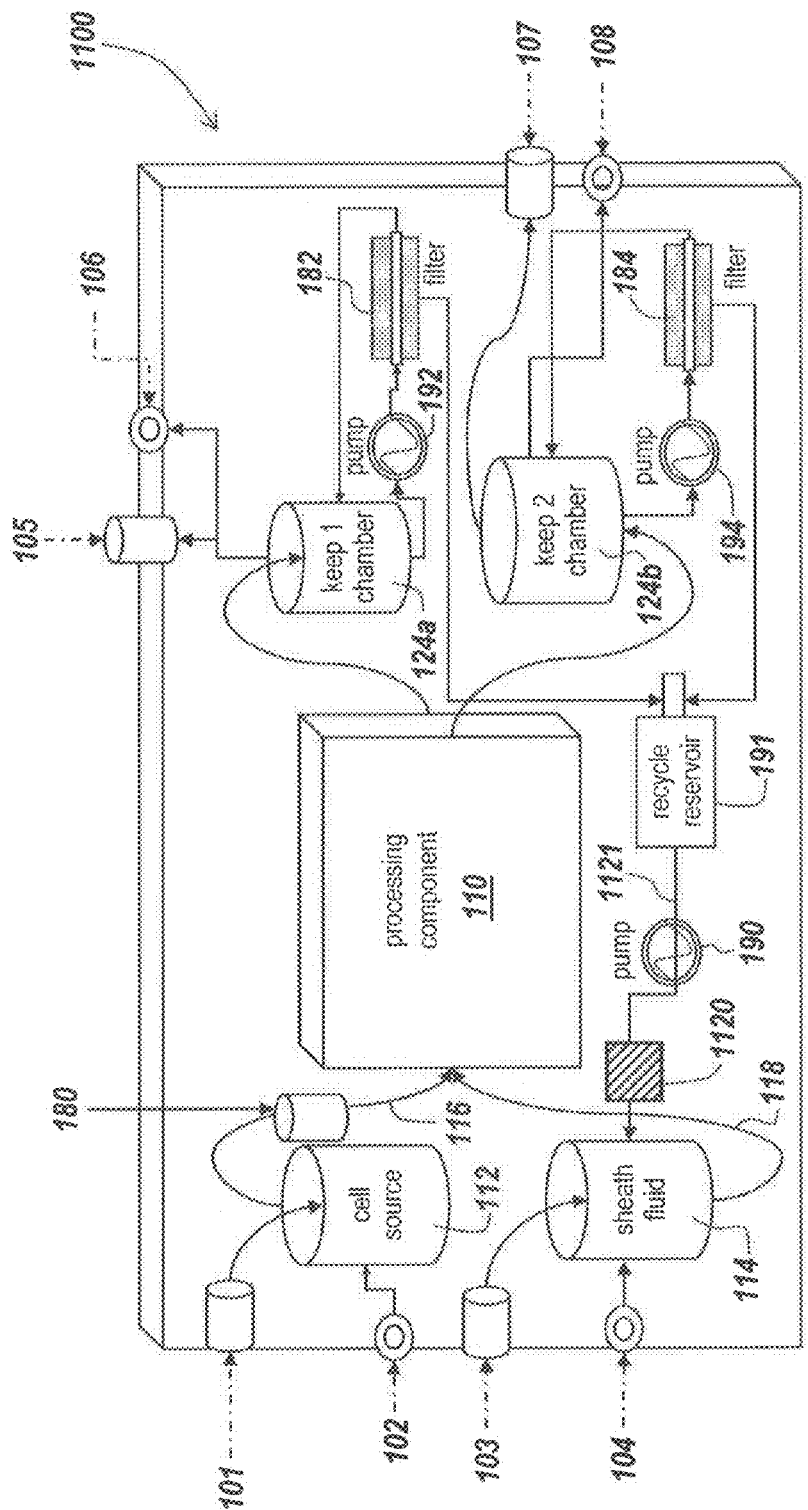
FIG. 7 illustrates an embodiment of a unitary particle processing cartridge of still another embodiment of the invention including a trap filter for filtering a recycling line from a recycle reservoir.

As shown in FIG. 7, a unitary particle processing cartridge 1100 of still another embodiment of the invention may include a trap filter 1120 for filtering a recycling line 1121 from a recycle reservoir 191. Preferably, the trap filter 1120 is selected to remove selected particles or molecules from the recycle line 1121.

The trapping filter 1120 may be removable from the cartridge 1100 to allow for further analysis of components trapped thereon. For example, in a cartridge that processes cells, the recycle reservoir 191 may receive supernatant pulled off of particles stored a processed particle chamber 124 by the filter 182 or 184. In one application, a sterile trapping filter, such as a 0.2 micron filter, may be used to trap microbes in the fluid in the recycling line 1121. The sterile trapping filter can subsequently be removed from the cartridge for microbial testing. In this manner, testing is more accurate and reflects a larger fraction of microbes present in a sample.

A sterile trapping filter may also be used to perform molecular cleaning of a sample flowing through the trapping filter 1120.

The trapping filter 1120 may alternatively comprise a plurality of beads for trapping certain components in the sample.

Figure 8:
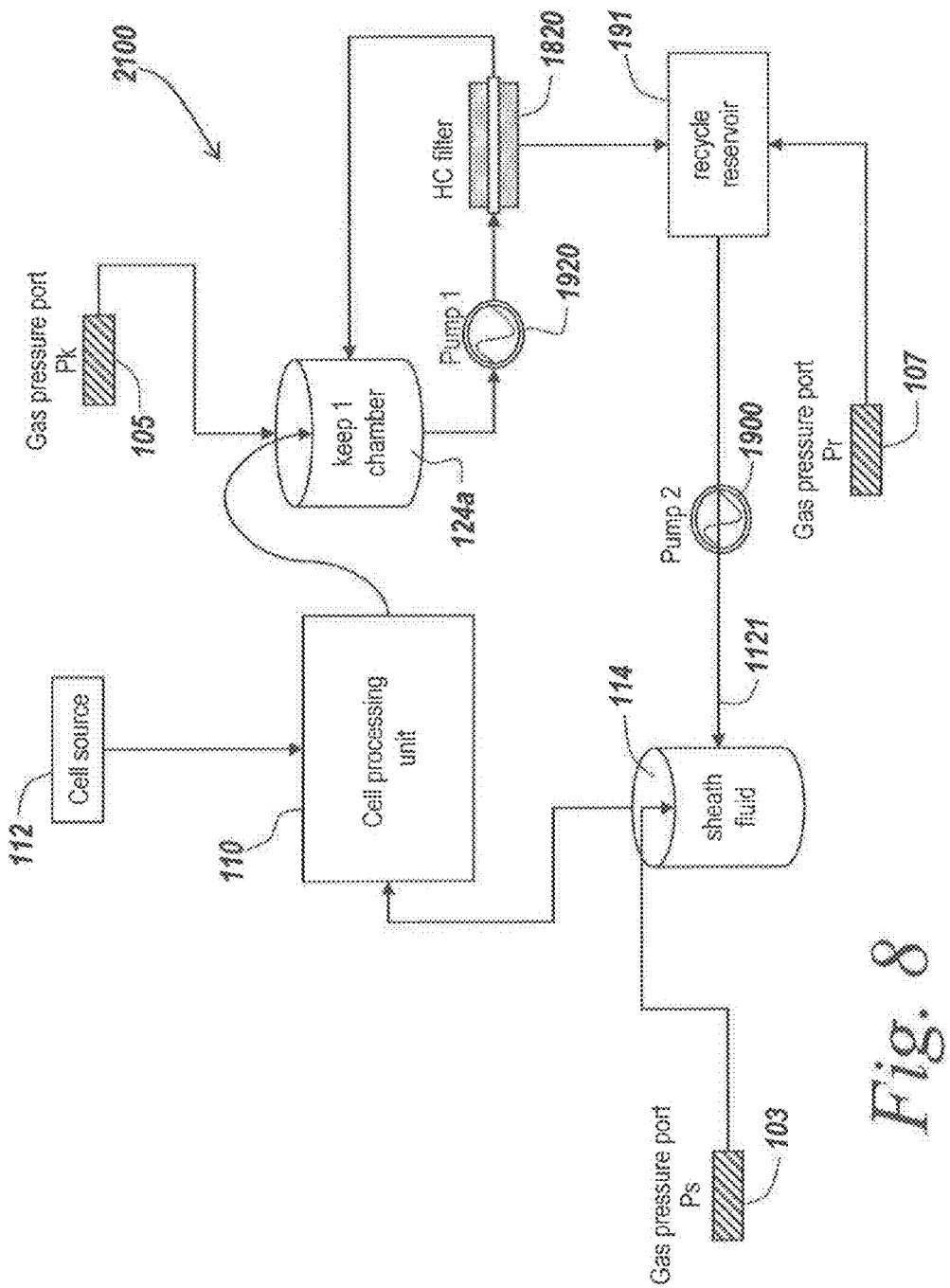
FIG. 8 illustrates another embodiment of a unitary particle processing cartridge according to the invention, including a pump-based supernatant recycling component.

FIG. 8 illustrates another embodiment of components of a unitary particle processing cartridge 2100 for processing cells according to the invention, including a pump-based supernatant recycling component. In the embodiment of FIG. 8, a simple supernatant recycling system uses a hollow core filter 1820 and two peristaltic pumps 1900, 1920. Cells passing through the cell processing system 110 emerge into the processed sample chamber 124a. Liquid containing cells is pumped through the core of the hollow core filter 1820 and back into the processed sample chamber 124a. Liquid, but no cells, can pass through the walls of the filter 1820 so liquid without cells is driven into the recycle reservoir 191. Preferably, the recycle reservoir 191 is maintained at atmospheric pressure using a gas pressure port 107, and the pump 1900 drives liquid (now without cells) into the sheath fluid reservoir 114 for re-use. The sheath fluid is driven by a regulated gas pressure into the cell processing system.

In the illustrative embodiment, the pressure of the unitary particle processing cartridge 2100 system Ps is relatively high, in order to drive sheath into the cell processing unit. The pressure of gas pressure ports 103, 105, which vent the processed sample chamber 124a and the recycle reservoir 191, respectively, are both regulated to atmospheric pressure.

Figure 9:
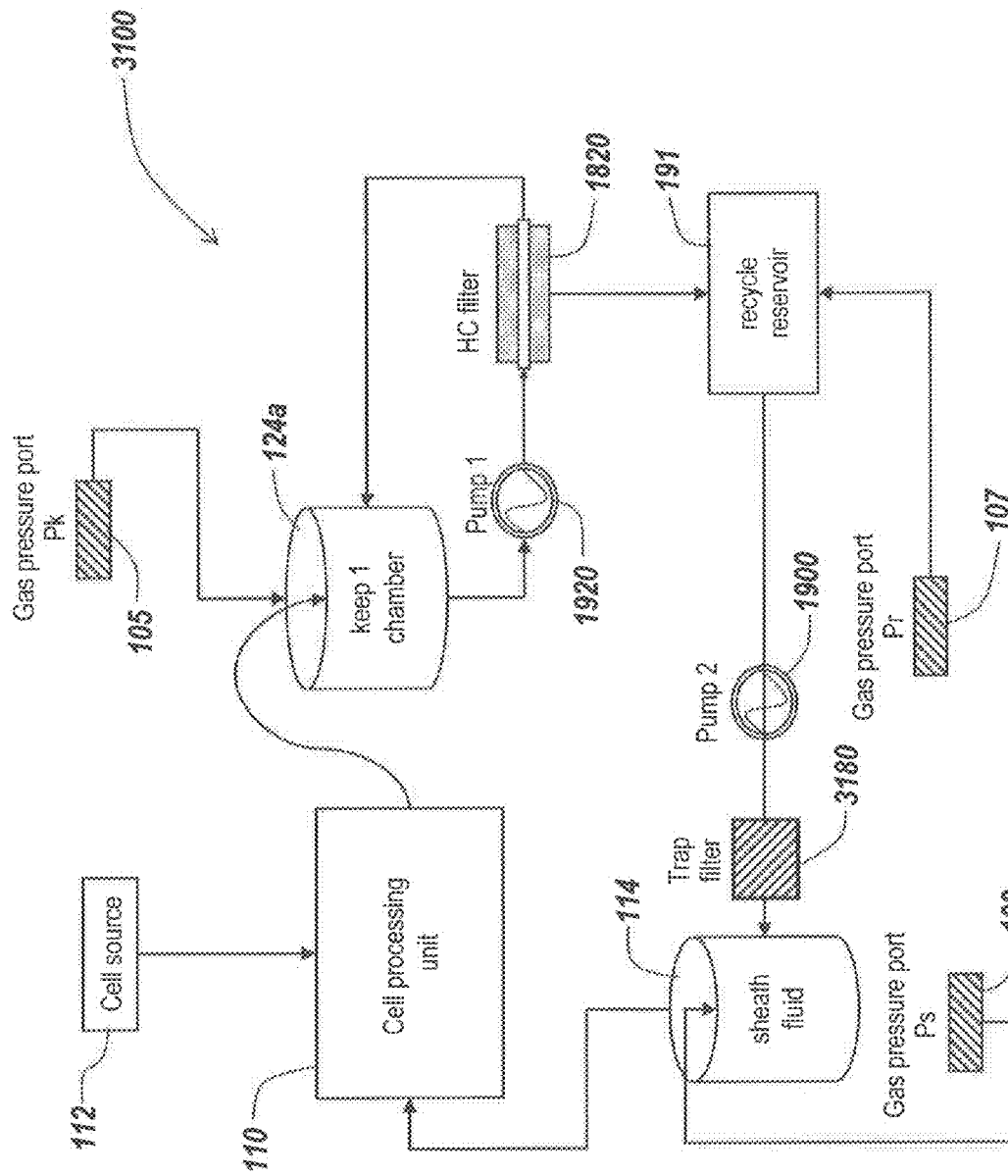
FIG. 9 illustrates a unitary particle processing cartridge of still another embodiment of the invention, including a pump-based supernatant recycling component.

According to another embodiment, shown in FIG. 9, a unitary particle processing cartridge 3100 including a pump-based supernatant recycling component may also include a trap filter 3180. In one embodiment, the trap filter 3180 may comprise a 0.2 um sterile mesh capable of trapping viruses and microbes. In that case as one cycles the system, a higher and higher percentage of liquid passes through that trap filter 3180, which collects a percentage of any microbes present in the initial cell source or sheath fluid.

Alternatively or at the same time, the trap filter 3180 used in a unitary particle processing cartridge may have molecular retention properties. For example, the trap filter may contain beads coated with protein G and protein A that bind immunoglobulins in the liquid that the system drives through the trap filter 3180. In such an embodiment, the cycling system "cleans" the liquid of any molecule which can be trapped by appropriate affinity binding beads.

A unitary particle processing cartridge employing such a trap filter may be used in several ways. For example, if the cell processing unit 110 is a simple mixing chamber and the initial sheath fluid contains anti-CD4 mouse antibody linked to a FITC fluorophore, the trap may contain bead-bound anti-mouse antibody and a 0.2 um filter to retain the beads. In such an embodiment, the system stains the input cells with the anti-CD4 antibody and then washes the stained cells to remove unbound antibody.

In another application, the trap filter 3180 may comprise a 0.2 um sterile filter made as a removable volume of about one milliliter. The trap filter traps any microbes in the original cell volume after sufficient cycling. From the point of detecting microbes in a batch of human cells in order to release the cells for use in cell therapy (bone marrow transplantation), a liter of cells may be used to then concentrate all the microbes into the one milliliter in the trap filter, allowing enhanced the concentration of any microbes by 1000$x$. Such a method makes conventional microbe detection assays much more rapid.

Figure 10:
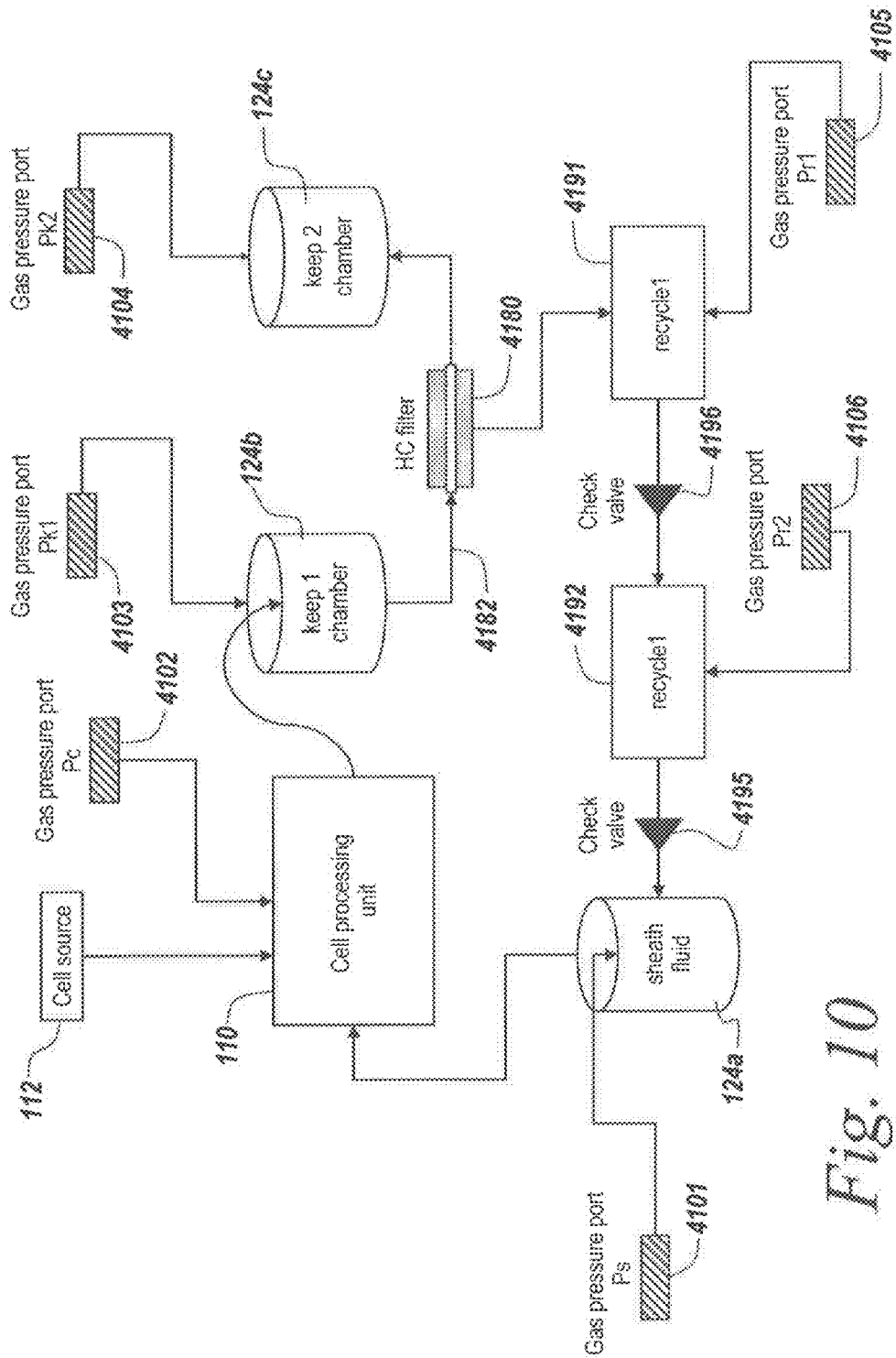
FIG. 10 illustrates a unitary particle processing cartridge including a pneumatic supernatant recycling system using a hollow core filter and no pumps.

According to still another embodiment of the invention, shown in FIG. 10, a unitary particle processing cartridge 4100 may include a pneumatic supernatant recycling system using a hollow core filter 4180 and no pumps. This subsystem of a cartridge has five chambers: a first processed sample chamber 124*a* (keep1), a second processed sample chamber 124*c* (keep2) coupled to the first processed sample chamber 124*a* via fluid path 4182, a first recycle chamber 4191 (recycle1), a second recycle chamber 4192 (recycle2), and a sheath chamber (sheath) 114.

All chambers are preferably at controlled pressures at all times. The pressures may be controlled using gas pressure ports 4101, 4102, 4103, 4104, 4105 and 4106 connected to the sheath chamber 114, the cell processing unit 110, the first processed sample chamber 124*a*, the second processed sample chamber 124*c*, the first recycle chamber 4191 and the second recycle chamber 4192, respectively. By controlling the flow resistances of the fluid paths (i.e., the tubing) between the chambers, the flow rate is therefore controlled. The cell processing unit 110 is maintained at an output pressure of Pc. The first processed sample chamber 124*a* is at a pressure of Pk1 which is below Pc.

The unitary particle processing cartridge 4100 has two flow states for the first processed sample chamber 124*a*, the second processed sample chamber 124*b* and the first recycle chamber 4191. In the first state, the pressure Pk1 of the first processed sample chamber is at a first level that is greater than the pressure Pk2 of the second processed sample chamber 124*c* and the pressure Pr1 of the first recycle chamber 4191, which are both zero. In a second state, the pressure Pk2 of the second processed sample chamber 124*c* is at a third level that is greater than the pressure Pk1 of the first processed sample chamber Pr1 and the pressure Pk2 of the first recycle chamber, which are both greater than zero.

In the first state, a sample comprising liquid containing cells flows from the first processed sample chamber 124*a* to the second processed sample chamber 124*c* through the core of the filter 4180. Supernatant from the sample flows through the wall of the filter 4180 into the first recycling chamber 4191.

In the second state, a sample comprising liquid containing cells flows from the second processed sample chamber 124*c* to the first processed sample chamber 124*a* and supernatant also flows through the wall of the filter into the first recycling chamber 4191.

In both states, the supernatant preferably has the same flow rate into the first recycling chamber 4191.

A control system, which is located off of the cartridge 4110, controls the pressures in the cartridge to oscillate between the first state and the second state in order to prevent the first or second processed sample chamber from either overflowing or draining.

The second recycle chamber 4192 is maintained at a pressure below the first recycling chamber 4191 until it is full, and is then switched to a pressure higher than both the first recycle chamber 4191 and sheath fluid chamber 114 in order to drive all liquid from the recycle chamber into the sheath fluid chamber 114. Then, the second recycling chamber 4192 is brought back to a pressure below the first recycling chamber 4191 to refill, and the sheath injection cycle repeats. Preferably, check valves 4195, 41976 are in place in the fluid paths between the first recycling chamber 4191, the second recycling chamber 4192 and the sheath fluid chamber 4114 to prevent backflow.

This system 4110 has few or no contact surfaces (i.e., peristaltic or other mechanical pumps) which may damage cells and so can improve yields of live cells.

Figure 11A:
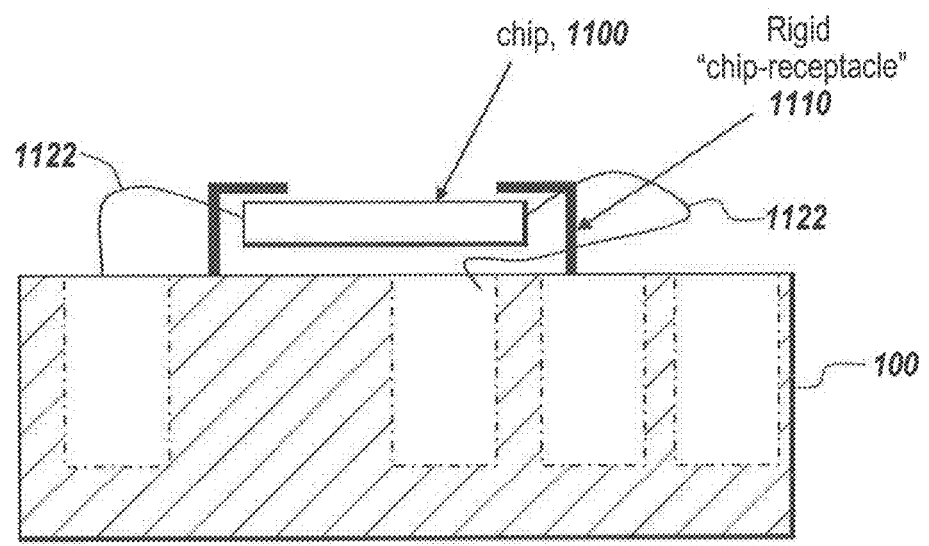
FIGS. 11A-11C illustrate unitary particle processing cartridge integrated with a multiwell plate according to one application of the invention.
Figure 11B:
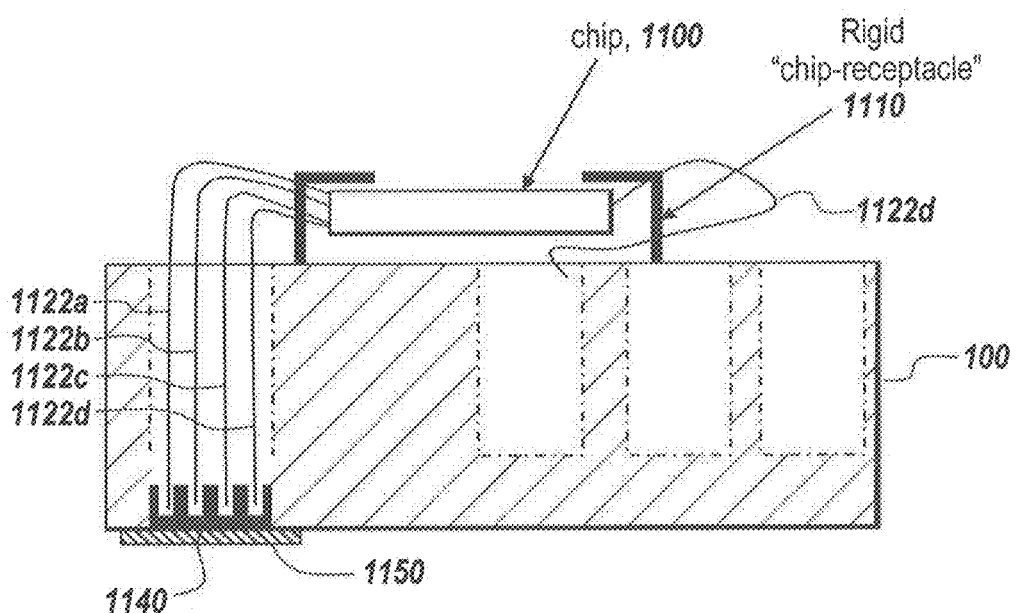
Figure 11C:
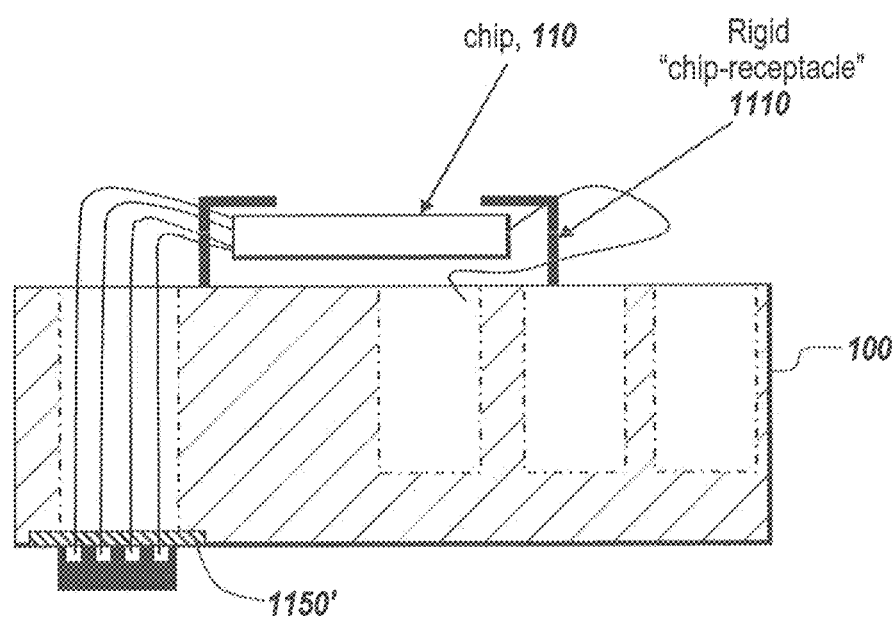

FIGS. 11A-11C illustrate a suitable application of the unitary particle processing cartridge of the illustrative embodiment of the invention. In the embodiment of FIGS. 11A-11C, a unitary cartridge 100 is integrated with a multiwell plate. FIG. 11A is a cross-sectional view of the cartridge, with chambers in a rigid body and a chip 1100 connected to the cartridge 100 through flexible tubes. The chip 1100 is stored for shipping and handling in a rigid "chip-receptacle" 1110 on the cartridge 100. The chip receptacle 1110 is sized and configured to receive and couple the chip 1100 to the cartridge.

In the illustrative embodiment, the chip 1100 may be a microfabricated glass chip as described in U.S. Pat. No. 6,808,075 and U.S. patent application Ser. Nos. 10/329,008 and 10/664,587, or a combination of a microfabricated chip in a non-microfabricated plastic package (chip holder) which are together stored in a rigid chip receptacle and slide out of that receptacle into the "Operating machine" for operation. The chip then moves back into the receptacle 1110 when the cell processing is done and the cartridge is removed for product extraction and disposal.

FIG. 11B shows an embodiment in which the chip 1100 has multiple input tubes 1122*a-e*. A well multi-well plate 1140, illustrated as containing four wells, though more or less may be used, is placed or connected to the cell input chamber in the cartridge, so that each tube receives cells from a different well of the multi-well plate 1140. In this embodiment, a pressure sealing plate 1150 may be used to seal the whole chamber so that a single driving pneumatic pressure is capable of driving multiple wells at once.

Alternatively, a sealing plate 1150' may be placed over the top of the wells of a multi-well plate, so that each well can be separately driven, as shown in FIG. 11C.

According to one embodiment, a multi-well plate may be clamped to a unitary particle processing cartridge so that each cell access tube 1122 is separately sealed onto each well, and the pressure in each well can be separately controlled. The system may include separate pneumatic control tubes to provide such separate control.

Multiwell variant cartridges are also very appropriate where a unit process in the cartridge is implemented with a chip that has parallelism. For example if the chip is an optical microsorter array of 96 microsorters, the system may route one microsorter to one well in a 96 well plate.

Figure 12A:
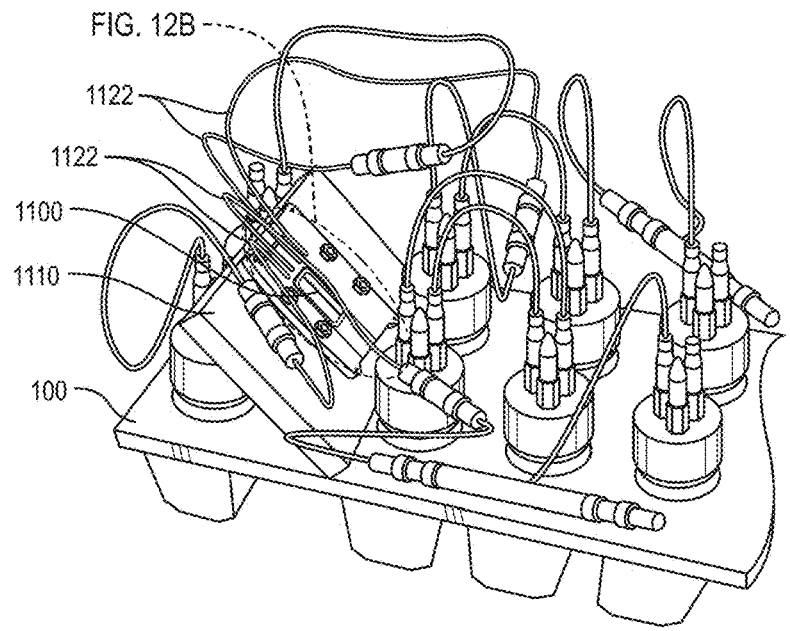
FIGS. 12A-12D are photographs of a prototype of a unitary particle processing cartridge of an illustrative embodiment of the invention.
Figure 12B:
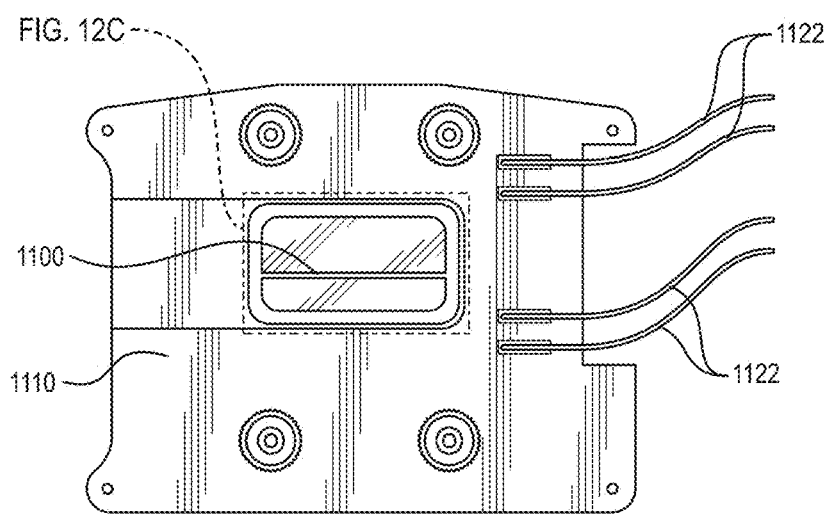
Figure 12C:
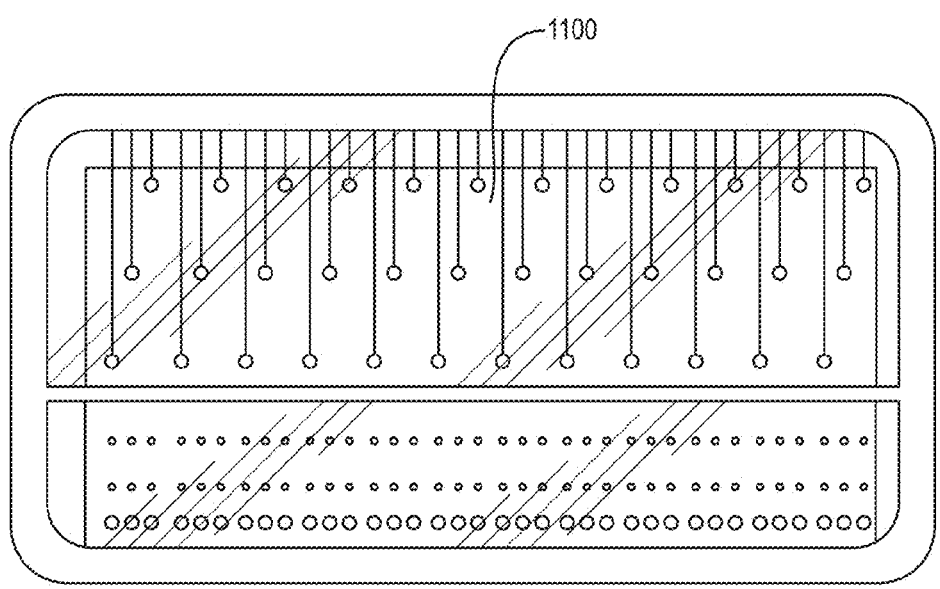
Figure 12D:
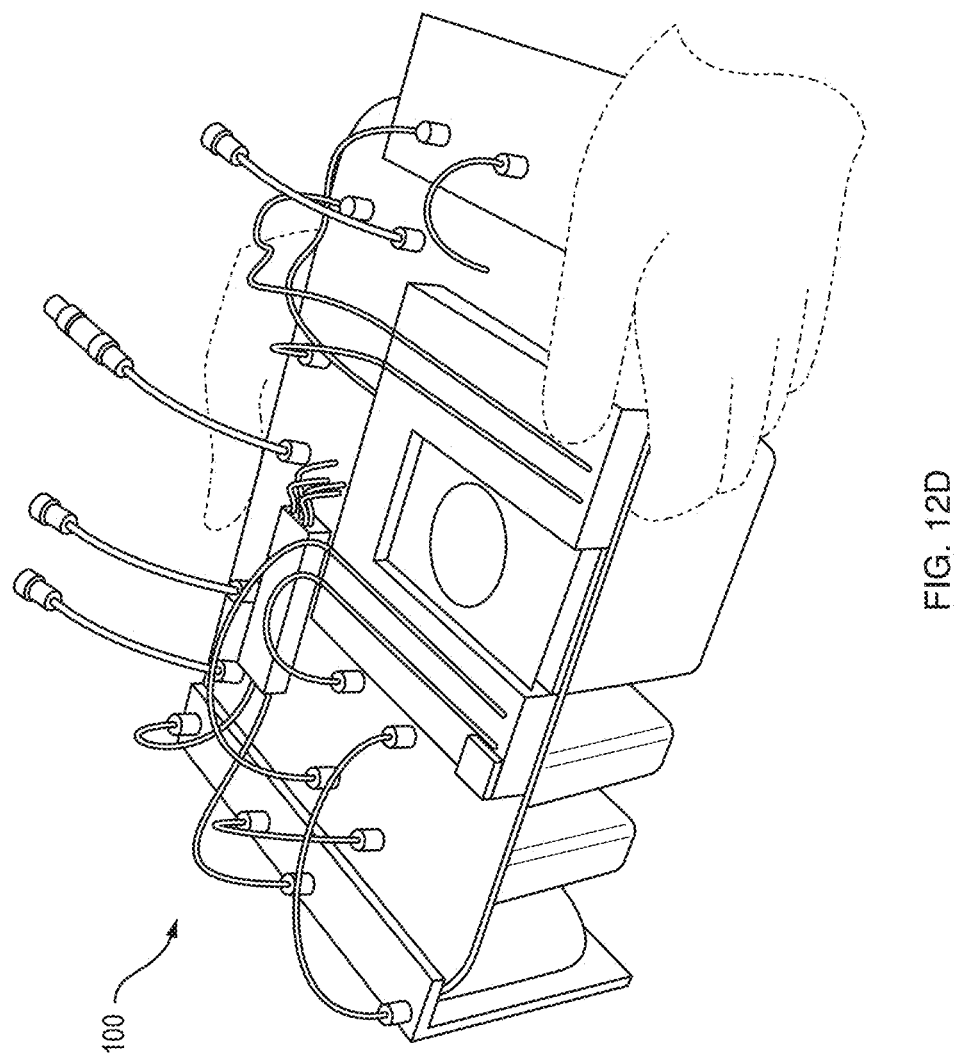

FIGS. 12A-12D are photographs of a prototype of a unitary particle processing cartridge of an illustrative embodiment of the invention. As shown in FIGS. 12A and 12B, a processing chip 1100 and a chip holder 1110 may be connected to a multi-chamber cartridge body 100 using flexible tubes 1122.

Figure 13:
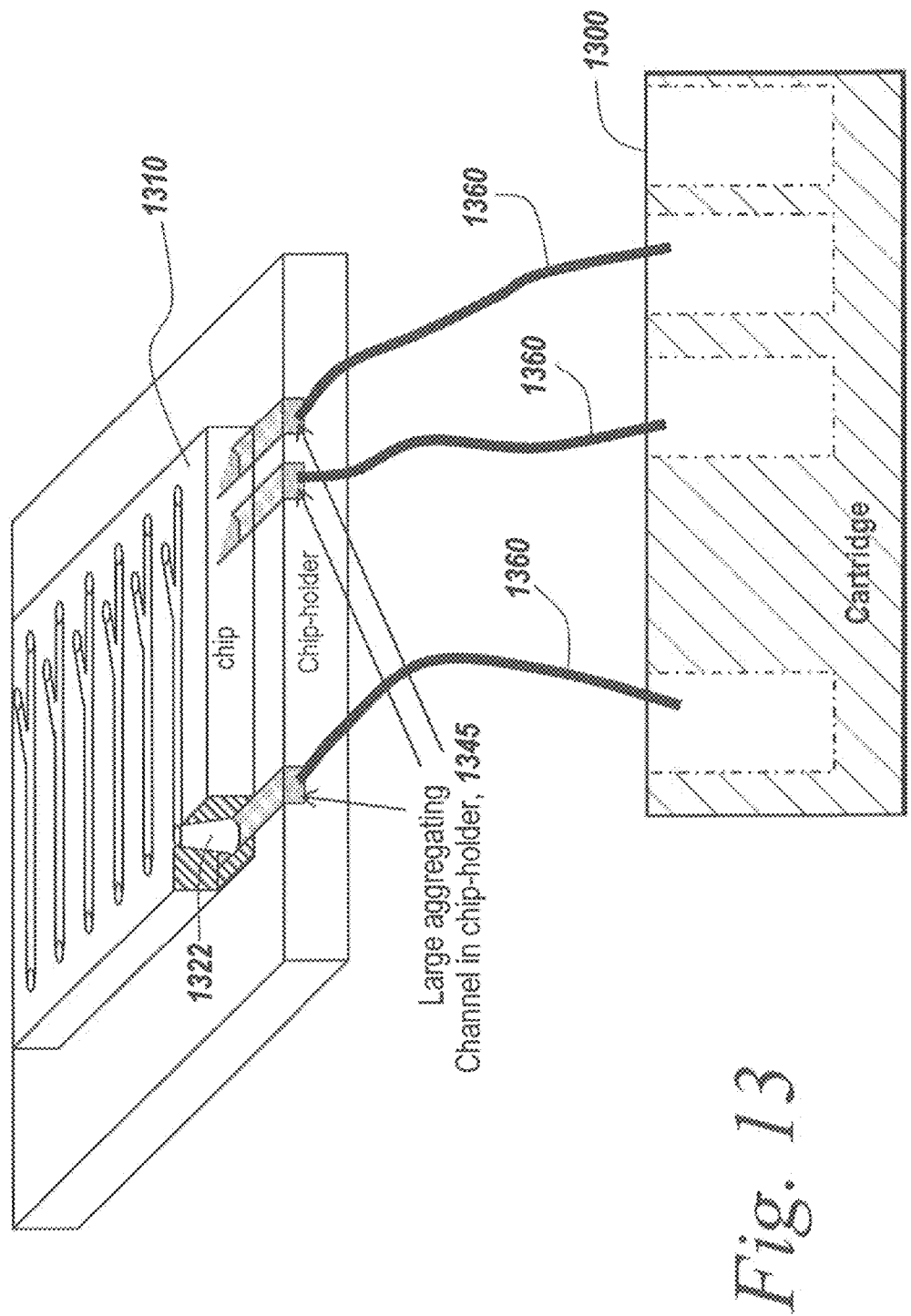
FIG. 13 illustrates another application of a unitary particle processing cartridge for processing particles, where the cartridge system allows for aggregation of a processed sample off-chip.

FIG. 13 illustrates another application of a unitary particle processing cartridge for processing particles. In the embodiment of FIG. 13, the cartridge system 1300 allows for aggregation of a processed sample off-chip. The illustrative chip 1310 contains an array of microchannels of a width scale of between about 10 µm and 400 µm. The chip holder 1340 for coupling the chip to the cartridge 1300 preferably contains chambers and tubes of a width scale of between about 100 µm to about 2 millimeters. The cartridge 1300 contains tubes of a width scale of between about 0.5 mm and about 10 mm and chambers of a volume scale of between about 1 millimeter and about 5000 millimeters.

FIG. 13 shows a cutaway portion of one channel 1322 of the chip 1310 for purposes of illustration only.

The chip holder 1340 includes aggregating chambers or channels 1345 for receiving a processed sample or input sample. The aggregating chambers 1345 connect to fluid paths, illustrated as flexible tubes 1360, preferably of equivalent or larger scale, which in turn feed to chambers 1334 in the cartridge 1300. Preferably, the chambers 1334 have volumes of between about 1 milliliter and about 5000 milliliters.

Alternatively, chambers on the chip holder 1340 may connect a channel on the chip 1310 to a chamber on the chip holder 1340, which then connects to a flexible tube or other fluid path. A plurality of the flexible tubes then aggregate into chambers in the cartridge.

The embodiment of FIG. 13 thus provides aggregation of separately processed, parallelized samples in a manner that reduces clogging.

In general, a unitary particle processing cartridge of an illustrative embodiment of the invention is a single object sealed against liquid transfer either in or out of the cartridge, except at specific ports that are only used in a specific standard operating procedure (SOP) that guarantees that their use does not violate the isolation of the interior of the cartridge or leak interior samples into the exterior.

In one embodiment, the unitary particle processing cartridge is operated by being placed in a machine or system (the "Operating Machine") which may apply means of actuation and sensing to the cartridge to perform one or more "unit process operations" on a suspension that has been loaded into the cartridge. The unit process operations performed using the cartridge may change the state of the suspension, measure some properties of the suspension, both change the state and measures selected properties of a suspension, or other perform another suitable process on a suspension loaded in the cartridge. Examples of unit processes suitable for use with the unitary cartridge of an illustrative embodiment of the invention include, but are not limited to, measuring the number of cells in a suspension, measuring the amount of liquid in a suspension, measuring the type of cells in a suspension, which may be a cytometry operation, sorting cells in the suspension, collecting a subset of the cells in a suspension, heating the cells in a suspension, filtering a suspension to increase the concentration of cells therein, and changing the liquid or its chemical components in a suspension.

The operating machine that operates on the unitary particle processing cartridge may use electrical, mechanical, pneumatic, optical, magnetic or other suitable actuation or sensing means known in the art to perform unit process operations on a suspension in the cartridge. Examples of actuation or sensing means suitable for use in an operating machine that employs the unitary cartridge of the illustrative embodiment of the invention include, but are not limited to, pneumatic means, mechanical means, optical means, magnetic means and electrical means. To actuate or sense using a pneumatic means, a gas may be injected through a sterile filter to drive a liquid suspension from one chamber to another or from a chamber through a component such as a size filter and into a second chamber. To actuate or sense using a mechanical means, a peristaltic pump head may be built into the cartridge so that an external rotor may fit into that head and by rotating it pump liquid or gas from one chamber to another. To actuate or sense using an optical means, a light beam may be disposed relative to the cartridge to pass through a microchannel in the cartridge in order to count cells or particles that pass through that microchannel and transiently block or scatter the light on its way to a photodetector. To actuate or sense using a magnetic means, a rotating magnet may be brought close to a chamber containing a conventional magnetic stir bar, causing that stir bar to rotate and stir or mix the suspension in that chamber. To actuate or sense using an electrical means, conventional silicon pressure or temperature sensors may be built into the cartridge and their electrical leads may be connected to through the means of external contact pins. The operating machine may then apply and read voltages to or from these contact pins to operate the sensors. Alternatively, using an electrical means, a data storage means, which may be part of a microcontroller or CPU, digital or analog, may be built into the cartridge if it is advisable for the cartridge itself to be given a logging function or intelligence function to support its use or standard operating procedures for handling the cartridge. Power for these devices may come from the operating machine or be derived from batteries or electrical power storage means located within the unitary cartridge. In another embodiment of a mechanical means for performing a process in a suspension loaded in a cartridge, two chambers may be connected by a tube with a region containing a soft wall to form a valve. Then, the operating machine may press on this region with a mechanical plate or other suitable means to temporarily or permanently crimp that region and selectively block liquid or gas flow from one chamber to another.

The use of the cartridge allows the operating machine to be isolated from and external to the processing subsystem and fluid contact surface. In this manner, the operating machine can be used repeatedly, while the fluid contact surfaces can be disposable.

The present invention enables customization of a unitary cartridge to optimize a cartridge for any given cell processing protocol by engineering into the cartridge only the required unit processes.

Chemical reagents, beads and/or particles that are either specific to the cell or particle processing protocol or independent of the protocol can be stored and shipped within the cartridge for processing by the user. Alternatively, the substances used in the selected process may be shipped separate from the cartridge and inserted in the cartridge by a technician at an intermediate stage, or a final user at an end stage.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A particle sorting system comprising:
   a cartridge including:
   a particle sorting component configured to receive a stream of particles and to individually sort on a particle-by-particle basis the stream of particles into selected particles having a predetermined characteristic and unselected particles not having the predetermined characteristic;
   a particle source upstream of and in fluid communication with the particle sorting component for providing particles to be sorted to the particle sorting component;
   a first chamber downstream of and in fluid communication with the particle sorting component for collecting the selected particles;
   a second chamber downstream of and in fluid communication with the particle sorting component for collecting unselected particles; and
   one or more sealing elements configured to completely seal the cartridge during a particle sorting operation so as to prevent liquid transfer to and from the interior of the cartridge.

2. The particle sorting system of claim 1, wherein the particle source is configured to provide particles to be sorted to the particle sorting component when an external source of pressure is applied to the particle source.

3. The particle sorting system of claim 1, further comprising:
   a sealable loading port formed in the cartridge for providing particles to the particle source chamber; and
   an extraction port formed in the cartridge for removing selected particles from the first chamber.

4. The particle sorting system of claim 1, further comprising a filter disposed in a fluid path of the cartridge.

5. The particle sorting system of claim 1, wherein the particle sorting component has a microfluidic flow channel configured to continuously flow particles therethrough, the microfluidic flow channel having a detection region configured to admit light to photodetect particles flowing through the flow channel.

6. The particle sorting system of claim 1, wherein the particle sorting component includes an optical micro sorter having a detection region, the detection region configured to allow light to interrogate individual particles for the predetermined characteristic, and wherein the optical microsorter individually sorts particles based on the predetermined characteristic.

7. The particle sorting system of claim 1, wherein the particle sorting component is manufactured separately and subsequently integrally joined to the remainder of the cartridge.

8. The particle sorting system of claim 1, wherein the particle sorting component is unitary and removable from the remainder of the cartridge.

9. The particle sorting system of claim 1, wherein the particle sorting component includes a plurality of microfluidic flow channels arranged in parallel, each of the plurality of microfluidic flow channels configured to continuously flow particles therethrough and configured to admit light to photodetect particles flowing through the microfluidic flow channels.

10. The particle sorting system of claim 1, wherein the cartridge further comprises:
    a sheath fluid reservoir for providing sheath fluid to suspend the particles to be sorted; and
    a sealable loading port formed in the cartridge for providing sheath fluid to the sheath fluid reservoir.

11. The particle sorting system of claim 1, wherein the cartridge includes all fluid contact surfaces required for a microfluidic particle sorting operation when the cartridge is operationally interfaced to a processing instrument.

12. The particle sorting system of claim 1, further comprising a plurality of sample processing units arranged to sequentially process a sample fluid containing the particles.

13. The particle sorting system of claim 1, wherein the particle sorting component includes a plurality of microchannels arranged in parallel, each of the plurality of microchannels having a first fluid path downstream of a sort region and a second fluid path downstream of a sort region.

14. The particle sorting system of claim 13, wherein the plurality of microchannels, including the first fluid paths and the second fluid paths, are arranged in the same plane.

15. The particle sorting system of claim 1, wherein the cartridge further includes one or more gas ports provided in at least one of the particle source chamber, the first chamber, and the second chamber.

16. The particle sorting system of claim 1, wherein the sorting component sorts particles without an aerosol phase.

17. The particle sorting system of claim 1, wherein the cartridge includes a chip receptacle configured to receive and couple the particle sorting component to the cartridge.

18. The particle sorting system of claim 1, wherein the cartridge is a single use, disposable cartridge.

19. The particle sorting system of claim 1, wherein the cartridge is sealed and all fluid contact surfaces within the cartridge are sterilized.

20. The particle sorting system of claim 1, wherein the cartridge is a rigid body.

21. The particle sorting system of claim 1, wherein the cartridge is a single object sealed against liquid transfer either in or out of the cartridge.

22. The particle sorting system of claim 1, wherein the cartridge is configured to be operationally interfaced to a processing instrument.

23. The particle sorting system of claim 1, wherein the cartridge is configured for insertion into a processing instrument, the processing instrument having an actuator for performing a processing operation on the stream of particles.

24. The particle sorting system of claim 1, further comprising a processing instrument configured to actuate the cartridge to perform a sorting operation on the stream of particles, and wherein the fluid contact surfaces of the cartridge are fluidically isolated from the processing instrument during the sorting operation.

25. The particle sorting system of claim 1, wherein the cartridge is provided with a unique identification.

26. The particle sorting system of claim 1, wherein the particle source includes a plurality of individual wells.

* * * * *